US009220705B2

(12) United States Patent
Hoeschele et al.

(10) Patent No.: US 9,220,705 B2
(45) Date of Patent: Dec. 29, 2015

(54) METHOD OF TREATING COLORECTAL CANCER

(71) Applicants: James David Hoeschele, Plymouth, MI (US); Nicola Margiotta, Barletta (IT); Valentina Gandin, Tarzo (IT); Emanuele Petruzzella, Molfetta (IT); Cristina Marzano, Padua (IT)

(72) Inventors: James David Hoeschele, Plymouth, MI (US); Nicola Margiotta, Barletta (IT); Valentina Gandin, Tarzo (IT); Emanuele Petruzzella, Molfetta (IT); Cristina Marzano, Padua (IT)

( * ) Notice: Subject to any disclaimer, the term of this patent is extended or adjusted under 35 U.S.C. 154(b) by 0 days.

(21) Appl. No.: 14/199,858

(22) Filed: Mar. 6, 2014

(65) Prior Publication Data

US 2014/0255394 A1 Sep. 11, 2014

Related U.S. Application Data

(60) Provisional application No. 61/774,073, filed on Mar. 7, 2013.

(51) Int. Cl.
| | | |
|---|---|---|
| A61K 31/28 | (2006.01) | |
| A61K 31/282 | (2006.01) | |
| C07F 15/00 | (2006.01) | |
| A61K 45/06 | (2006.01) | |

(52) U.S. Cl.
CPC ............... *A61K 31/282* (2013.01); *A61K 45/06* (2013.01); *C07F 15/0093* (2013.01)

(58) Field of Classification Search
USPC ....................................................... 514/492
See application file for complete search history.

(56) References Cited

U.S. PATENT DOCUMENTS

| 4,999,444 A * | 3/1991 | Hoeschele et al. ............ 556/137 |
| 5,393,909 A | 2/1995 | Khokhar et al. |
| 5,434,256 A | 7/1995 | Khokhar et al. |

FOREIGN PATENT DOCUMENTS

| JP | 63017894 A | 1/1988 |
| WO | 03024978 | 3/2003 |

OTHER PUBLICATIONS

Margiotta et al. CAS: 157: 373813, 2012.*
Chen et al. CAS: 158: 203565, 2013.*
Hoeschele et al., J. Med. Chem,. 1994, 37: 2630-2636.*
Dara, S.C., A Rapid Method for the Synthesis of cis-[Pt(NH3)2Cl2], Indian Journal of Chemistry, 1970, 8, pp. 193-194.
Kidani, Y., et al., Antitumor Activity of 1, 2-Diaminocyclohexane-Platinum Complexes against Sarcoma-180 Ascites Form, Journal of Medicinal Chemistry, 1978, 21(12), pp. 1315-1318.
Khokhar, A.R., et al., Synthesis and X-ray crystal structure of cis-1,4-diaminocyclohexanetetrachloroplatinum (IV): a new antitumor agent, Inorganica Chimica Acta, 1994, 219, pp. 193-197.
Hoeschele, J.D., et al., Synthesis, Structural Characterization, and Antitumor Properties of a Novel Class of Large-Ring Platinum (II) Chelate Complexes Incorporating the cis-1,4-Diaminocyclohexane Ligand in a Unique Locked Boat Conformation, Journal of Medicinal Chemistry, 1994, 37, pp. 2630-2636.
Shamsuddin, S., et al., Synthesis, Characterization, and Antitumor Activity of a Series of Novel Cisplatin Analogs with cis-1,4-Diaminocyclohexane as Nonleaving Group, Journal of Inorganic Biochemistry, 1996, 61, pp. 291-301.
Shamsuddin, S., et al., Synthesis and Characterization of Novel Axial Dichloroplatinum (IV) Cisplatin Analogues: Crystal Structure of an Axial Dichloro Complex [Pt(cis-1,4-DACH) (trans-Cl2) (CBDCA)]. 1/2 MeOH, Inorganic Chemistry, 1997, 36, pp. 5969-5971.
Shamsuddin, S., Synthesis, characterization, and antitumor activity of new platinum (IV) trans-carboxylate complexes: Crystal structure of [Pt (cis-1,4-DACH) trans-(acetate)2Cl2], Journal of Inorganic Biochemistry, 1998, 71, pp. 29-35.
Rounaq Ali Khan, S., et al., Synthesis and Characterization of New Cis-1,4-Diaminocyclohexane and Piperidine Platinum (II) Complexes Containing Disubstituted Sulfide Groups, Journal of Coordination Chemistry, 2000, 51, pp. 323-333.
Ali, M.S., et al., cis-1,4-Diaminocyclohexane-Pt (II) and -(IV) adducts with DNA bases and nucleosides, Journal of Inorganic Biochemistry, 2003, 96, pp. 452-456.
Shamsuddin, S., et al., Synthesis characterization and X-ray crystal structure of cis-1,4-diaminocyclohexane-platinum (II) nucleobase adducts, Polyhedron, 2007, 26, pp. 637-644.
Ranaldo, R., et al., Conformer Distribution in (cis-1,4-DACH) bis (guanosine-5'-phosphate) platinum (II) Adducts: A Reliable Model for DNA Adducts of Antitumor Cisplatin, Inorganic Chemistry, 2008, 47, pp. 2820-2830.
Kasparkova, J., et al., Cytotoxcity, cellular uptake, glutathione and DNA interactions of an antitumor large-ring Pt II chelate complex incorporating the cis-1,4-diaminocyclohexane carrier ligand, Biochemical Pharmacology, 2010, 79, pp. 552-564.
Margiotta, N., et al., Platinum-bisphosponate complexes have proven to be interactive chemotherapeutics targeted for maligant mesothelioma because of inappropriate hydrolysis, Journal of Inorganic Biochemistry, 2011, 105, pp. 548-557.
Margiotta, N., et al., Cationic intermediates in oxidative addition reactions of Cl2 to [PtCl2(cis-1,4-DACH)], Dalton Transactions, 2011, 40, pp. 12877-12885.

(Continued)

*Primary Examiner* — Rei-Tsang Shiao
(74) *Attorney, Agent, or Firm* — Francis J. Tinney

(57) ABSTRACT

The present invention relates to the use of certain platinum compounds including [PtCl$_2$(cis-1,4-diaminocyclohexane)], or combinations of these compounds with a variety of other agents for treating and/or preventing the progression of colorectal cancer in mammals. In particular, the invention provides methods of treating and/or preventing oxaliplatin-refractory colorectal cancer in mammals.

11 Claims, 5 Drawing Sheets

(56) References Cited

OTHER PUBLICATIONS

Margiotta, N., et al., Revisiting [PtCl2 (cis-1,4-DACH)]: An Underestimated Antitumor Drug with Potential Application to the Treatment of Oxaliplatin-Refractory Colorectal Cancer, Journal of Medicinal Chemistry, 2012, 55, pp. 7182-7192.

Brabec, Y., et al., Thermodynamic and Mechanistic Insights into Translesion DNA Synthesis Catalyzed by Y-Family DNA Polymerase Across a Bulky Double-Base Lesion of an Antitumor Platinum Drug, Chemistry A European Journal, 2012, 18, pp. 15439-15448.

* cited by examiner

Cisplatin

Carboplatin

Oxaliplatin

[PtCl$_2$(1R,2R-DACH)] (2)

[PtCl$_2$(cis-1,4-DACH)] (1)

METHOD OF TREATING COLORECTAL CANCER

FIELD OF THE INVENTION

The present invention relates to the use of certain platinum compounds or combinations of these compounds with a variety of other therapeutic agents for treating and/or preventing the progression of colorectal cancer in mammals. In particular, the invention provides methods of treating and/or preventing oxaliplatin-refractory colorectal cancer in mammals.

BACKGROUND OF THE INVENTION

Platinum drugs (cisplatin, cis-diamminedichloroplatinum (II), CDDP; carboplatin, diammine[1,1-cyclobutanedicarboxylato]platinum(II); and oxaliplatin, [(1R,2R)-cyclohexane-1,2diamine](ethanedioato)platinum(II); FIG. 1) are widely used in the clinic and the prototype cisplatin still represents an antineoplastic drug with highly curative effects in a solid malignancy such as testicular cancer (*Cisplatin: Chemistry and Biochemistry of a Leading Anticancer Drug*. (Lippert, B., Eds.). Verlag Helvetica Chimica Acta, Zürich, 2000, 563 pp.; Jakupec, M. A., et al., *Dalton Trans.* 2008, 183-194; Kelland, L., *Nat. Rev. Cancer* 2007, 7, 573-584; Reedijk, J., *Eur. J. Inorg. Chem.* 2009, 1303-1312; Wong, E., et al., *Chem. Rev.* 1999, 99, 2451-2466; Hall, M. D., et al., *J. Med. Chem.* 2007, 50, 3403-3411; and Wheate, N. J., et al., *Dalton Trans.* 2010, 39, 8113-8127). The complex [PtCl$_2$(cis-1,4-DACH)] (DACH=diaminocyclohexane), [SP-4-2-(cis)]-dichloro(1,4-cyclohexanediamine-N,N')platinum, compound 1 (FIG. 1), contains an isomeric form of the diaminocyclohexane ligand found in oxaliplatin and has been widely investigated as a potential new platinum anticancer drug. Compound 1 also called "Kiteplatin" based on its structural features (Ranaldo, R., et al., *Inorg. Chem.* 2008, 47, 2820-2830) resembling a parachute (the cis-1,4-DACH ligand) on a skydiver (the metal). U.S. Pat. No. 4,999,444 discloses a series of novel neutral mixed ligand platinum (II) and platinum (IV) complexes including [SP-4-2-(cis)]-dichloro(1,4-cyclohexanediamine,N,N')platinum.

The first paper reporting the in vitro and in vivo activities of compound 1 was published by Hoeschele, J. D., et al, *J. Med. Chem.* 1994, 37, 2630-2636. The in vitro growth inhibition data indicated that compound 1 exhibited potent activity in sensitive L1210 and P388 cell lines and that the compound also appeared more potent than cisplatin (based on ID$_{50}$ values) against all tested Pt-resistant cell lines with the only exception of the cisplatin-resistant cell lines L1210PtR4 and L1210DDP5 (partial cross-resistance) and the oxaliplatin-resistant cell line L1210DACH. In vivo, compound 1 proved to be more dose potent than cisplatin (based on % T/C values) against the parental L1210 and P388 murine leukemias. Compound 1 also retained a significant activity against sublines derived from L1210 and P388 and made resistant to cisplatin. Both compound 1 and cisplatin produced equivalent activity against B16 melanoma and M5076 sarcoma, while cisplatin was more active than compound 1 against colon carcinoma 26 at equitoxic doses. These initial data suggested that the spectrum of activity of compound 1 could have been different from those of cisplatin and oxaliplatin.

Two years later, Shamsuddin, S., et al., *J. Inorg. Biochem.* 1996, 61, 291-301 reported the in vitro cytotoxicity of compound 1 against murine leukemia L1210 and human ovarian cancer A2780 cells. The compound was found to be more active than cisplatin and tetraplatin (Pt$^{IV}$Cl$_4$(1R,2R-DACH)) in both cell lines (the human A2780 cell line being more sensitive). The high potency and the high solubility in water of compound 1 made this compound an ideal lead for further studies. Khokhar and collaborators also explored Pt$^{IV}$(cis-1,4-DACH) derivatives (Shamsuddin, S., et al., *J. Inorg. Biochem.* 1998, 71, 29-35) and found that, among a series of complexes having the general formula cis,cis,trans-[Pt$^{IV}$Cl$_2$(cis-1,4-DACH)L$_2$] (L=CH$_3$(CH$_2$)$_n$COO—, n=0-8), cis,cis,trans-[Pt$^{IV}$Cl$_2$(cis-1,4-DACH)(CH$_3$COO)$_2$] was the most active in the murine L1210 leukemia model. Khokhar and colleagues also prepared and characterized monofunctional (Ali, M. S., et al., *J. Inorg. Biochem.* 2003, 96, 452-456) and bifunctional (Shamsuddin, S., et al., *Polyhedron.* 2007, 26, 637-644) adducts of compound 1 with nucleobases as models for DNA binding of these Pt antitumor drugs (Wang, D., et al., *Nat. Rev. Drug Discovery* 2005, 4, 307-320 and Fuertes, M. A., et al., *Chem. Rev.* 2003, 103, 645-662).

A peculiar feature of platinum-coordinated cis-1,4-DACH is the formation of a seven-membered chelate ring, which is larger than the usually encountered five- and six-membered rings (X-ray diffraction data) (Hoeschele, J. D., et al, *J. Med. Chem.* 1994, 37, 2630-2636 and Ranaldo, R., et al., *Inorg. Chem.* 2008, 47, 2820-2830). This results in a very large bite angle ($\geq 97°$ that could affect mobility of cis ligands. Indeed researchers investigated the (cis-1,4-DACH)PtG$_2$ system (G=two untethered guanine bases) (Ranaldo, R., et al., *Inorg. Chem.* 2008, 47, 2820-2830) and by lowering the temperature, were able to observe the presence of different rotamers in solution (two HT, head-to-tail, and one HH, head-to-head, conformers are possible in aqueous solution) (Natile, G., et al., *Coord. Chem. Rev.* 2006, 250, 1315-1331 and references therein).

The unique antitumor activity of compound 1 was further investigated with reference to: cell entry, reaction with sulfur-containing compounds, binding to DNA, and processing of DNA adducts by proteins (including DNA repair enzymes) (Kasparkova, J., et al., *Biochem. Pharmacol.* 2010, 79, 552-564). In particular, compared to cisplatin, compound 1 revealed: i) improved cytotoxicity (3.4-5.4-fold greater) and enhanced cellular uptake (ca. 1.5-fold greater) in human ovarian A2780 cancer cell line; ii) enhanced rate but similar sequence preference for DNA binding in cell-free media; iii) identical DNA interstrand cross-linking efficiency (6%); iv) similar bending (32°) but enhanced local DNA unwinding (ca. 1.5-fold greater) for 1,2-GG-intrastrand cross-links; v) markedly enhanced inhibition of DNA polymerase accompanied by significantly lower efficiency of DNA repair.

Later, in order to determine how the Y-family translesion DNA polymerase η (Polη) processes lesions generated by complex 1, model systems employing a DNA double-base lesion derived from 1,2-GG intrastrand crosslinks of this complex were investigated (V. Brabec, J. Malina, N. Margiotta, G. Natile, J. Kasparkova. *Chem. Eur. J.* 2012, 18, 15439-15448). The catalytic efficiency of Polη for the insertion of correct dCTP, with respect to the other incorrect nucleotides, opposite the 1,2-GG cross-link was markedly reduced by the cis-1,4-DACH carrier ligand. This reduced efficiency of Polη to incorporate the correct dCTP could be due to a more extensive DNA unstacking and deformation of the minor groove induced in the DNA by the cross-link of bulky complex 1. The major products of the bypass of this double-base lesion produced by complex 1 by Polη resulted from misincorporation of dATP opposite the platinated G residues. The results of the investigation supported the thesis that the misincorporation could be due to sterical effects of the bulkier cis-1,4-DACH ligand hindering the formation of the Polη-DNA-incoming nucleotide complex. Calorimetric analysis suggested also that thermodynamic factors may contribute to the forces that governed enhanced incorporation of the incorrect dATP by Polη as well.

Colorectal cancer is at the top of the list of the most common cancers worldwide, with around 1 million new cases diagnosed every year (Van Cutsem, E., et al., *J. Clin. Oncol.* 2007, 25, 1658-1664). Early stage colorectal cancer is frequently curable with surgery, but the appearance of metastases leads to unresectable tissues with fatal consequences for the patient (Saltz, L. B., et al., *J. Clin. Oncol.* 2004, 22, 1201-1208). The best outcome in the therapy of metastatic colorectal cancer is obtained by the use of 5-fluorouracil, oxaliplatin, and irinotecan. More recently, biologic therapies have also proved to be effective in prolonging the median survival time (Sobrero, A. F., et al., *J. Clin. Oncol.* 2008, 26, 2311-2319).

Presently, apart from oxaliplatin, there are no other drugs in advanced clinical development which appear to be active against colorectal cancer and that could be used for the treatment of patients with oxaliplatin-refractory colorectal cancer.

Thus, there is considerable interest and an urgent need to find therapies to treat and or prevent oxaliplatin-refractory colorectal cancer. The present invention answers the need by providing compounds of formula I and formula II and in particular compound 1. Therefore, compound 1 was evaluated against human colorectal cancer cells and, in particular, colorectal cancer cells resistant to oxaliplatin (Margiotta, N., et al., *J. Med. Chem.* 2012, 55(16), pp 7182-7192). We surprisingly and unexpectedly found that compounds of formula I and formula II and in particular compound 1 was effective in treating refractory colorectal cancer and especially in circumventing cisplatin and oxaliplatin resistance in colorectal cancer.

SUMMARY OF THE INVENTION

In one embodiment, the present invention provides a method of treating refractory colorectal cancer in a mammal in need of such treatment comprising administering to said mammal a therapeutically effective amount of a compound of formula I Formula I

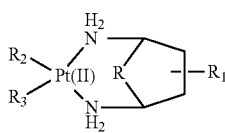

wherein R is —$(CH_2)_n$— in which n is an integer from one to three;

$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and $R_2$ and $R_3$ are negatively charged monodentate ligands which may be the same or different and are selected from the group consisting of chloro, bromo, iodo, hydroxo, nitrato, nitrito, acetato and dichloroacetato or $R_2$ and $R_3$ taken together form a dinegatively charged bidentate ligand selected from the group consisting of sulfato, oxalato,

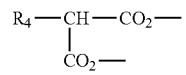

in which $R_4$ is hydrogen, hydroxyl, or an alkyl group of from one to four carbon atoms,

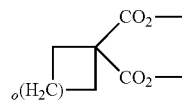

in which o is an integer from one to three and

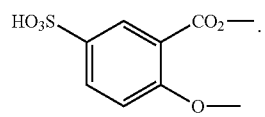

In another embodiment of the present invention R is —$(CH_2)_n$—, in which n is an integer from two to three; $R_1$ is hydrogen, carboxyl, an alkyl group of from one to four carbon atoms or an alkoxy group of from one to four carbon atoms; and $R_2$ and $R_3$ are negatively charged monodentate ligands which may be the same or different and are selected from the group consisting of chloro and bromo or $R_2$ and $R_3$ taken together form a dinegatively charged bidentate ligand selected from the group consisting of

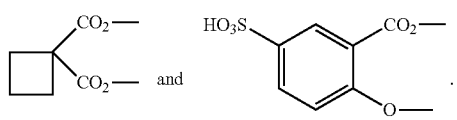

In another embodiment of the present invention $R_1$ is hydrogen, carboxyl, methyl, or methoxy.

In another embodiment of the present invention a compound of formula I is selected from the group consisting of:
[SP-4-2-(cis)]-dichloro(1,4-cyclohexanediamine-N,N')platinum;
[SP-4-2-(cis)]-dichloro(1,3-cyclohexanediamine-N,N')platinum;
[SP-4-2-(cis)]-dichloro(1,4-cycloheptanediamine-N,N') platinum;
[SP-4-2-(cis)]-[1,1-cyclobutanedicarboxylato-(2-)O,O$^1$](1, 4-cyclohexanediamine-N,N')platinum;
[SP-4-2-(cis)]-(1,4-cyclohexanediamine-N,N') [2-hydroxy-5-sulfobenzoato (3)-O$^1$,O$^2$]platinate (1-), hydrogen; and
[SP-4-2-(cis)]-(1,4,cyclohexanediamine-N,N')[ethanedioato (2)-O,O$^1$]platinum.

In another embodiment of the present invention a compound of formula I is

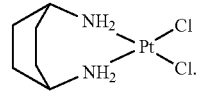

In another embodiment of the present invention a compound of formula I is

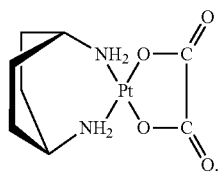

In another embodiment, the present invention provides a method of treating refractory colorectal cancer in a mammal in need of such treatment comprising administering to said mammal a pharmaceutical composition comprising a therapeutically effective amount of compound of formula I

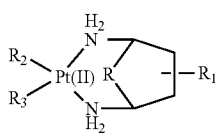

Formula I wherein R is —$(CH_2)_n$— in which n is an integer from one to three;
$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and
$R_2$ and $R_3$ are negatively charged monodentate ligands which may be the same or different and are selected from the group consisting of chloro, bromo, iodo, hydroxo, nitrato, nitrito, acetato and dichloroacetato or $R_2$ and $R_3$ taken together form a dinegatively charged bidentate ligand selected from the group consisting of sulfato, oxalato,

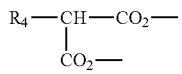

in which $R_4$ is hydrogen, hydroxyl, or an alkyl group of from one to four carbon atoms,

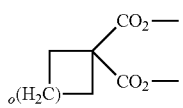

in which o is an integer from one to three and

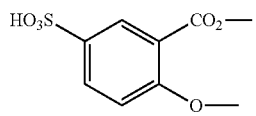

and at least one carrier, diluent or excipient.

In another embodiment, the present invention provides a method of treating refractory colorectal cancer in a mammal in need of such treatment comprising administering to said mammal a therapeutically effective amount of a compound of formula I

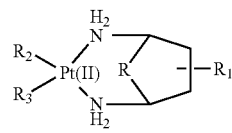

Formula I wherein R is —$(CH_2)_n$— in which n is an integer from one to three;
$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and
$R_2$ and $R_3$ are negatively charged monodentate ligands which may be the same or different and are selected from the group consisting of chloro, bromo, iodo, hydroxo, nitrato, nitrito, acetato and dichloroacetato or $R_2$ and $R_3$ taken together form a dinegatively charged bidentate ligand selected from the group consisting of sulfato, oxalato,

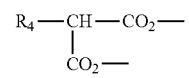

in which $R_4$ is hydrogen, hydroxyl, or an alkyl group of from one to four carbon atoms,

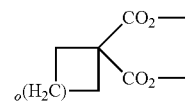

in which o is an integer from one to three and

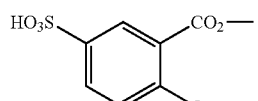

and at least one second therapeutic agent useful in treating colorectal cancer selected from the group consisting of: capecitabine; cetuximab; bevacizumab; a MEK inhibitor; a FOLFOX4 dosing schedule consisting of oxaliplatin, 5-fluorouracil and leucovorin; and a FOLFIRI dosing schedule consisting of irinotecan, 5-fluorouracil and leucovorin.

In another embodiment, the present invention provides a method of treating refractory colorectal cancer in a mammal in need of such treatment comprising administering to said mammal a therapeutically effective amount of a compound of formula I and a MEK inhibitor which is N-[(R)-2,3-dihydroxy-propoxy]-3,4-difluoro-2-(2-fluoro-4-iodo-phenylamino)-benzamide, or a pharmaceutically acceptable salt thereof.

In another embodiment, the present invention provides a method of treating refractory colorectal cancer in a mammal in need of such treatment comprising administering to said mammal a pharmaceutical composition comprising a therapeutically effective amount of a compound of formula I

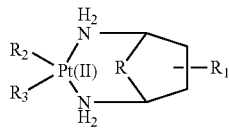

Formula I wherein R is —$(CH_2)_n$— in which n is an integer from one to three;

$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and $R_2$ and $R_3$ are negatively charged monodentate ligands which may be the same or different and are selected from the group consisting of chloro, bromo, iodo, hydroxo, nitrato, nitrito, acetato and dichloroacetato or $R_2$ and $R_3$ taken together form a dinegatively charged bidentate ligand selected from the group consisting of sulfato, oxalato,

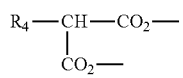

in which $R_4$ is hydrogen, hydroxyl, or an alkyl group of from one to four carbon atoms,

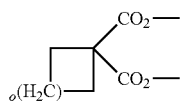

in which o is an integer from one to three and

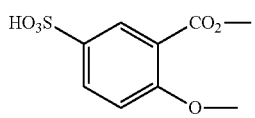

and at least one second therapeutic agent useful in treating colorectal cancer selected from the group consisting of: capecitabine, cetuximab, bevacizumab, a MEK inhibitor, a FOLFOX4 dosing schedule consisting of oxaliplatin, 5-fluorouracil and leucovorin and a FOLFIRI dosing schedule consisting of irinotecan, 5-fluorouracil and leucovorin and at least one carrier, diluent or excipient.

In another embodiment, the present invention provides a method of treating refractory colorectal cancer in a mammal in need of such treatment comprising administering to said mammal a therapeutically effective amount of a compound of formula II

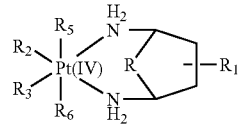

Formula II wherein R is —$(CH_2)_n$— in which n is an integer from one to three;

$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and $R_2$ and $R_3$ are negatively charged monodentate ligands which may be the same or different and are selected from the group consisting of chloro, bromo, iodo, hydroxo, nitrato, nitrito, acetato and dichloroacetato or $R_2$ and $R_3$ taken together form a dinegatively charged bidentate ligand selected from the group consisting of sulfato, oxalato,

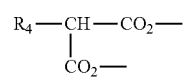

in which $R_4$ is hydrogen, hydroxyl, or an alkyl group of from one to four carbon atoms,

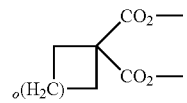

in which o is an integer from one to three and

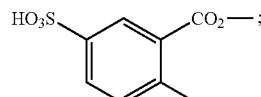

and $R_5$ and $R_6$ are negatively charged monodentate ligands which may be the same or different and are selected from the group consisting of chloro, bromo, iodo, hydroxo, nitrato, nitrito, benzoato, 3,4,5-trihydroxybenzoato, 3,4,5-trimethoxybenzoato, $R_7(CH_2)_p$—$CO_2$— wherein $R_7$ is selected from the group consisting of methyl, trifluoromethyl, $CH_2Cl$, $CH_2Br$, $CH_2F$, $CHCl_2$, $CHBr_2$ and $CHF_2$ and p is zero or an integer of one to five and $R_7(CH_2)_q$—O— wherein $R_7$ is defined above and q is zero or an integer of one to five.

In another embodiment of the present invention in a compound of Formula II R is —$(CH_2)_n$—, in which n is an integer from two to three; $R_1$ is hydrogen, carboxyl, an alkyl group of from one to four carbon atoms or an alkoxy group of from one to four carbon atoms; and $R_2$ and $R_3$ are negatively charged monodentate ligands which may be the same or different and are selected from the group consisting of chloro and bromo or $R_2$ and $R_3$ taken together form a dinegatively charged bidentate ligand selected from the group consisting of

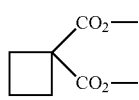 and 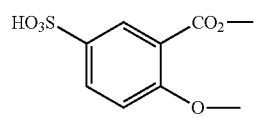.

In another embodiment of the present invention in a compound of Formula II $R_1$ is hydrogen, carboxyl, methyl, or methoxy.

In another embodiment of the present invention a compound of formula II is selected from the group consisting of:

(OC-6-33)-dichloro(cis-1,4-cyclohexanediamine-N,N')bis-dichloroacetateplatinum;

[OC-6-22-(cis)]-tetrachloro(1,4-cyclohexanediamine-N,N')platinum;

(OC-6-33)-dichloro(cis-1,4-cyclohexanediamine-N,N')dihydroxyplatinum;

(OC-6-33)-[ethanedioato(2)-O,O'](cis-1,4-cyclohexanediamine-N,N')dihydroxyplatinum; and (OC-6-33)-[ethanedioato(2)-O,O'](cis-1,4-cyclohexanediamine-N,N')bisdichloroacetateplatinum.

In another embodiment of the present invention a compound of formula II is

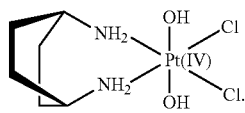

In another embodiment of the present invention a compound of formula II is

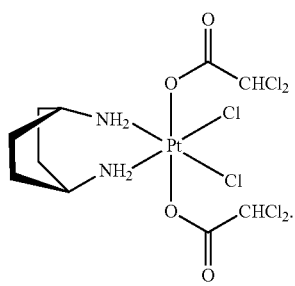

In another embodiment of the present invention a compound of formula II is

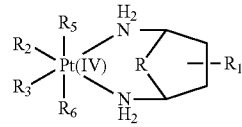

In another embodiment of the present invention a compound of formula II is

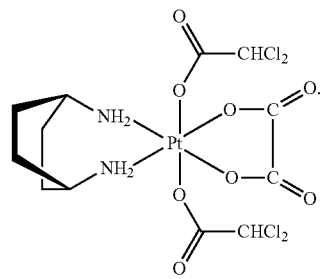

In another embodiment, the present invention provides a method of treating refractory colorectal cancer in a mammal in need of such treatment comprising administering to said mammal a pharmaceutical composition comprising a therapeutically effective amount of a compound of formula II Formula II

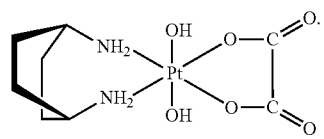

wherein R is —$(CH_2)_n$— in which n is an integer from one to three;

$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and $R_2$ and $R_3$ are negatively charged monodentate ligands which may be the same or different and are selected from the group consisting of chloro, bromo, iodo, hydroxo, nitrato, nitrito, and acetato and dichloroacetato or $R_2$ and $R_3$ taken together form a dinegatively charged bidentate ligand selected from the group consisting of sulfato, oxalato,

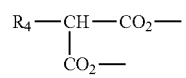

in which $R_4$ is hydrogen, hydroxyl, or an alkyl group of from one to four carbon atoms,

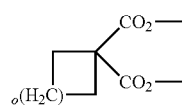

in which o is an integer from one to three and

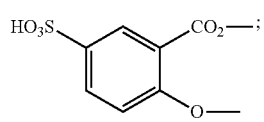;

and $R_5$ and $R_6$ are negatively charged monodentate ligands which may be the same or different and are selected from the group consisting of chloro, bromo, iodo, hydroxo, nitrato, nitrito, benzoato, 3,4,5-trihydroxybenzoato, 3,4,5-trimethoxybenzoato, $R_7(CH_2)_p$—$CO_2$— wherein $R_7$ is selected from the group consisting of methyl, trifluoromethyl, $CH_2Cl$, $CH_2Br$, $CH_2F$, $CHCl_2$, $CHBr_2$ and $CHF_2$ and p is zero or an integer of one to five and $R_7(CH_2)_q$—O— wherein $R_7$ is defined above and q is zero or an integer of one to five and at least one carrier, diluent or excipient.

In another embodiment, the present invention provides a method of treating refractory colorectal cancer in a mammal in need of such treatment comprising administering to said mammal a therapeutically effective amount of a compound of formula II

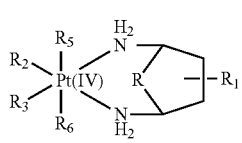

Formula II wherein R is —$(CH_2)_n$— in which n is an integer from one to three;

$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and $R_2$ and $R_3$ are negatively charged monodentate ligands which may be the same or different and are selected from the group consisting of chloro, bromo, iodo, nitrato, nitrito, acetato and dichloroacetato or $R_2$ and $R_3$ taken together form a dinegatively charged bidentate ligand selected from the group consisting of sulfato, oxalato,

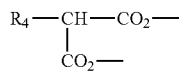

in which $R_4$ is hydrogen, hydroxyl, or an alkyl group of from one to four carbon atoms,

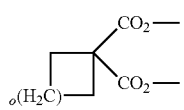

in which o is an integer from one to three and

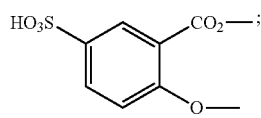

and $R_5$ and $R_6$ are negatively charged monodentate ligands which may be the same or different and are selected from the group consisting of chloro, bromo, iodo, hydroxo, nitrato, nitrito, benzoato, 3,4,5-trihydroxybenzoato, 3,4,5-trimethoxybenzoato, $R_7(CH_2)_p$—$CO_2$— wherein $R_7$ is selected from the group consisting of methyl, trifluoromethyl, $CH_2Cl$, $CH_2Br$, $CH_2F$, $CHCl_2$, $CHBr_2$ and $CHF_2$ and p is zero or an integer of one to five and $R_7(CH_2)_q$—O— wherein $R_7$ is defined above and q is zero or an integer of one to five and at least one second therapeutic agent useful in treating colorectal cancer selected from the group consisting of: capecitabine; cetuximab; bevacizumab; a MEK inhibitor; a FOLFOX4 dosing schedule consisting of oxaliplatin, 5-fluorouracil and leucovorin; and a FOLFIRI dosing schedule consisting of irinotecan, 5-fluorouracil and leucovorin.

In another embodiment, the refractory colorectal cancer is oxaliplatin-refractory colorectal cancer.

In another embodiment, the present invention is directed to treating a human.

Additionally, another embodiment of the present invention is a compound having the following structure

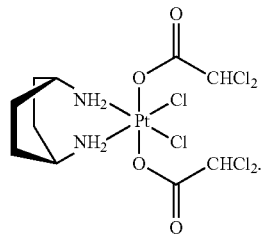

Additionally, another embodiment of the present invention is a compound having the following structure

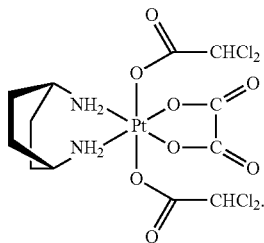

DETAILED DESCRIPTION OF THE INVENTION

Figure 1:
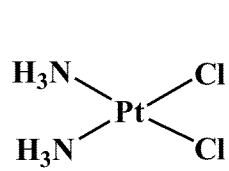
FIG. 1: Structures of Cisplatin, Carboplatin, Oxaliplatin, [PtCl$_2$(1R,2R-DACH)] (Compound 2), and [PtCl$_2$(cis-1,4-DACH)] (Compound 1).
Figure 1:
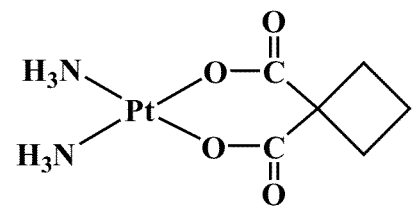
Figure 1:
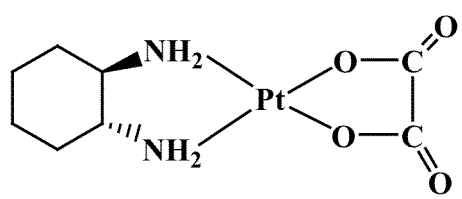
Figure 1:
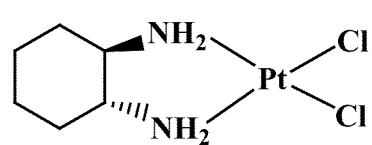
Figure 1:
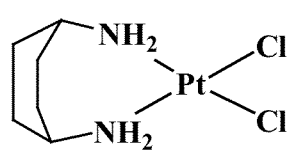

In the compounds of Formula I and II the term "alkyl" means a straight or branched chain hydrocarbon group having from one to ten carbon atoms and includes for example, methyl, ethyl, n-propyl, isopropyl, n-butyl, isobutyl, tertiary butyl, n-pentyl, n-hexyl, n-heptyl, n-octyl, nonyl, and the like.

"Alkoxy" is O-alkyl in which alkyl is as defined above.

"Cycloalkyl" means a saturated hydrocarbon ring having three to six carbon atoms and includes, for example, cyclopropyl, cyclobutyl, cyclopentyl, cyclohexyl, and the like.

"Hydroxyalkyl" means a hydroxy group attached to an alkyl radical in which alkyl is as defined above.

"Halogen" is iodine, bromine, fluorine and chlorine.

The term "mammal" refers to mice, rats, rabbits, guinea pigs, sheep, goats, cats, dogs, monkeys etc. Preferably, the term "mammal" refers to humans.

The term "treating" refers to having a therapeutic effect and at least partially alleviating or abrogating an abnormal condition such as colorectal cancer. Preferably, "treating" refers to having a therapeutic effect in refractory colorectal cancer and more preferably "treating" oxaliplatin-refractory colorectal cancer.

The term "preventing" refers to decreasing the probability that a mammal including a human contracts or develops colorectal cancer. Preferably, "preventing" refers to decreasing the probability that a mammal including a human contracts or develops refractory colorectal cancer and more preferably "preventing" oxaliplatin-refractory colorectal cancer.

The term "refractory colorectal cancer" refers to a mammal including a human who is either initially unresponsive to therapy or who becomes unresponsive to therapy over time.

The term "oxaliplatin-refractory colorectal cancer" refers to a mammal including a human who failed to respond to oxaliplatin-based therapy or whose disease has progressed after such treatment.

Abbreviation Used in the Application

DACH=diaminocyclohexane; DMSO=Dimethyl sulfoxide; DMF=dimethylformamide; GF-AAS=Graphite Furnace Atomic Absorption Analysis; HH=Head-to-Head; HT=Head-to-Tail; $IC_{50}$=half-maximum inhibitory concentration; MM/QM=Molecular Mechanics/Quantum Mechanics; MRD=Multi-Drug Resistant; MRP=Multi-drug Resistance Protein; NER=Nucleotide Excision Repair; PBS=Phosphate Buffered Saline; P-gp=P-glycoprotein; RF=Resistance Factor; RP-HPLC=Reverse Phase High-Pressure Liquid Chromatography; S.D.=Standard Deviation; THF=tetrahydrofuran.

The neutral mixed ligand platinum complexes/compounds of formula I and formula II are restricted to the cis-geometric isomers. Complexes of formula I and formula II may also possess asymmetric carbon atoms (chiral centers) and thus the racemates, individual enantiomer as well as mixtures of enantiomers are also included within the scope of the invention.

The compounds of the invention may exist in both unsolvated and solvated forms. The term 'solvate' is used herein to describe a molecular complex comprising a compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

The invention also includes isotopically-labeled compounds, which are identical to a compound of formula I or formula II, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, chlorine and platinum such as $^2H$, $^3H$, $^{13}C$, $^{14}C$, $^{15}N$, $^{18}O$, $^{17}O$, $^{36}Cl$, $^{191}Pt$ and $^{195m}Pt$ respectively. Compounds of the present invention, which contain the aforementioned isotopes and/or other isotopes of other atoms, are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. An isotopically labeled compound of formula I or II of the invention can generally be prepared by carrying out the procedures described for the non-labeled compounds, substituting a readily available isotopically labeled reagent for a non-isotopically labeled reagent.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see Haleblian, J. K., *Journal of Pharmaceutical Sciences,* 1975, 64 (8), 1269-1288), the disclosure of which is incorporated herein by reference in its entirety.

Compounds of Formula I and Formula II may be prepared according to the procedures described in the literature. See for example U.S. Pat. No. 4,999,444; Hoeschele, J., et al., *J. Med. Chem.* 1994, 37, 2630-2636; Shamsuddin, S., *Inorg. Biochem.* 1996, 61, 291-301; Ranaldo, R., et al., *Inorg. Chem.* 2008, 47, 2820-2830; Dhara, S. C., *Indian J. Chem.* 1970, 8, 193-194; and Shamsuddin, S., *J. Inorg. Biochem.* 1998, 71, 29-35.

Combination Therapy

The present invention also provides combinations, methods of using combinations and kits for use in combination therapies, using a compound of formula I or formula II and a variety of other therapeutic agents.

In one embodiment, the present invention provides a method of treating refractory colorectal cancer in a mammal in need of such treatment comprising administering to said mammal a therapeutically effective amount of a compound of formula I or II and at least one second therapeutic agent useful in treating colorectal cancer. For example, the second therapeutic agent may be selected from the group consisting of:

capecitabine; cetuximab; bevacizumab; a MEK inhibitor such as N-[(R)-2,3-dihydroxy-propoxy]-3,4-difluoro-2-(2-fluoro-4-iodo-phenylamino)-benzamide, or a pharmaceutically acceptable salt thereof; a FOLFOX4 dosing schedule consisting of oxaliplatin, 5-fluorouracil and leucovorin; and a FOLFIRI dosing schedule consisting of irinotecan, 5-fluorouracil and leucovorin and the like. Effective dosages of a second therapeutic agent(s) would be known to one skilled in the art (see for example Physicians' Desk Reference 67th ed. 2013) and if needed may be further varied at the discretion of the prescribing physician.

Pharmaceutical Compositions

The compounds of the present invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a pharmaceutically acceptable carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang, A. C. and Chen, L. H., *Expert Opinion on Therapeutic Patents*, 2001, 11 (6), 981-986, the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980, the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described for example in U.S. Pat. No. 6,106,864. Details of other suitable release technologies such as high energy dispersions and osmotic and coated particles can be found, for example in Verma, R. K. and Garg, S., *Pharmaceutical Technology On-line*, 2001, 25(2), 1-14. The use of chewing gum to achieve controlled release for example is described in WO 00/35298. The disclosures of these references are incorporated herein by reference in their entireties.

Additionally, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound.

Examples of such formulations include drug-coated stents and poly lactic-co-glycolic acid (PLGA) microspheres.

Also, the compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, Finnin, B. C. and Morgan, T. M., *Journal of Pharmaceutical Sciences*, 1999, 88 (10), 955-958. Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Compounds of the invention may also be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Finally, compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Inasmuch as it may desirable to administer a combination of active compounds, for example, for the purpose of treating and/or preventing refractory colorectal cancer, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

The compounds of formula I and II are valuable anticancer agents. Thus, the anticancer activity of representative compounds of formula I and II were compared to other known anticancer platinum compounds in various in vitro and in vivo assays.

A. In Vitro Assays

1. Cell Cultures

Human breast (MCF-7) and colon (HCT-15, DDL1, SW480 and CaCo-2) carcinoma cell lines along with melanoma (A375) were obtained from the American Type Culture Collection (ATCC, Rockville, Md.). A431 are human cervical carcinoma cells kindly provided by Prof. F. Zunino (Molecular Pharmacology Unit, Experimental Oncology and Molecular Medicine, Istituto Nazionale dei Tumori, Milan, Italy). 2008 and its cisplatin resistant variant, C13*, are human ovarian cancer cell lines kindly provided by Prof. G. Marverti (Dept. of Biomedical Science, University of Modena, Italy). LoVo human colon-carcinoma cell line and its multidrug-resistant sublime (LoVo MDR) were kindly provided by Prof F. Maj one (Department of Biology of Padova University, Italy). The LoVo-OXP cells were derived using a standard protocol in which LoVo cells were grown in increasing concentrations of oxaliplatin and resistant clones were selected over a period of nine months (Gaudin, V., et al., *J. Cell. Mol. Med.* 2012, 16, 142-151). Cell lines were maintained in the logarithmic phase at 37° C. in a 5% carbon dioxide atmosphere using the following culture media containing 10% fetal calf serum (Euroclone, Milan, Italy), antibiotics (50 units $mL^{-1}$ penicillin and 50 μg $mL^{-1}$ streptomycin), and 2 mM L-glutamine in: i) RPMI-1640 medium (Euroclone) for MCF-7, HCT-15, A431, DLD 1, 2008, and C13* cells; ii) F-12 HAM'S (Sigma Chemical Co.) for LoVo, LoVo MDR, and LoVo-OXP cells; iii) DMEM for A375 and SW 480 cells; and iv) MEM for CaCo-2 cells.

2. Cytotoxicity Assay

The growth inhibitory effect towards tumor cell lines was evaluated by means of the MTT (3-(4,5-dimethylthiazol-2-yl)-2,5-diphenyltetrazolium bromide) assay (Alley, M. C., et al., *Cancer Res.* 1988, 48, 589-601).

Briefly, depending upon the growth characteristics of the cell line, 3-8×$10^3$ cells $well^{-1}$, were seeded in 96-well microplates in growth medium (100 μL) and then incubated at 37° C. in a 5% carbon dioxide atmosphere. After 24 h, the medium was removed and replaced with a fresh one containing the compound to be studied, at the appropriate concentration, dissolved in 0.9% sodium chloride solution just before use. Triplicate cultures were established for each treatment. After 72 h, each well was treated with 10 mL of a 5 mg $mL^{-1}$ MTT saline solution and, after 5 h of incubation, 100 μL of a sodium dodecylsulfate (SDS) solution in 0.01 M HCl were added. After an overnight incubation, the inhibition of cell growth induced by the tested complexes was determined by measuring the absorbance of each well at 570 nm using a BioRad 680 microplate reader. Mean absorbance for each drug dose was expressed as percentage of the control and plotted vs. drug concentration. Dose-response curves were fitted and $IC_{50}$ values were calculated with four parameter logistic model (4PL). $IC_{50}$ values represent the drug concentrations that reduce the mean absorbance at 570 nm to 50% of those in the untreated control wells.

3. Cytotoxicity

Compound 1 was prepared for the first time almost twenty years ago however, until now, it had been tested (both in vitro and in vivo) only in a limited number of tumor cell lines (Hoeschele, J. D., et al., *J. Med. Chem.* 1994, 37, 2630-2636 and Shamsuddin, S., et al., *J. Inorg. Biochem.* 1996, 61, 291-301). The Pt(II) and Pt(IV) complexes containing isomeric forms of diaminocyclohexane, [$PtCl_2$(cis-1,4-DACHA](1), [$PtCl_2$(1R,2R-DACH)] (2), [Pt(OXA)(cis-1,4-DACH)] (3), cis,trans,cis-[$Pt^{IV}Cl_2(OH)_2$(cis-1,4-DACH)] (4), cis,trans,cis-[$Pt^{IV}Cl_2(DCA)_2$(cis-1,4-DACH)] (5), [Pt(CBDCA)(cis-1,4-DACH)] (6), cis,trans,cis-[$Pt^{IV}$(OXA)(OH)$_2$(cis-1,4-DACH)] (7), and cis,trans,cis-[$Pt^{IV}$(OXA)(DCA)$_2$(cis-1,4-DACH)] (8) were evaluated for their cytotoxic activity towards a panel of human tumor cell lines including cervical (A431), breast (MCF-7), cancers along with a melanoma (A375) and 4 different colon cancer cell lines corresponding to different stages of the disease progression (HCT-15, SW480, CaCo-2, DLD-1). The cytotoxicity was evaluated by means of the MTT test for 72 h treatment with increasing concentrations of the tested compounds. For comparison purposes, the cytotoxicity of cisplatin, the most widely used anticancer metallodrug, and oxaliplatin, key drug in FOLFOX (Folinic acid, 5-Fluorouracil & Oxaliplatin) regimens for the treatment of colorectal cancers, were evaluated in the same experimental conditions. $IC_{50}$ values, calculated from dose-survival curves, are shown in Table 1.

TABLE 1

In vitro antitumor activity[a]

| Cell line | Tissue type | $IC_{50}$ (μM) ± S.D. Compound[b] | | | | | |
|---|---|---|---|---|---|---|---|
| | | 1 | 2 | 3 | 4 | 5 | 6 |
| HCT-15 | colon | 2.66 ± 0.95 | 8.02 ± 1.84 | 12.23 ± 1.76 | 10.32 ± 1.42 | 3.16 ± 1.06 | 31.85 ± 3.48 |
| SW480 | colon | 2.12 ± 0.87 | 11.12 ± 2.05 | 7.42 ± 1.75 | 6.32 ± 2.15 | 3.02 ± 1.05 | 26.83 ± 2.87 |
| CaCo-2 | colon | 1.27 ± 0.65 | 16.26 ± 2.97 | 6.65 ± 1.25 | 7.12 ± 3.13 | 2.02 ± 0.84 | 39.44 ± 3.35 |
| DLD-1 | colon | 4.97 ± 0.53 | 8.06 ± 2.11 | 8.86 ± 1.11 | 7.74 ± 2.16 | 5.12 ± 0.94 | 29.76 ± 2.75 |
| MCF-7 | breast | 3.09 ± 1.06 | 9.52 ± 2.36 | 10.32 ± 2.41 | 7.01 ± 2.05 | 4.74 ± 1.15 | 20.87 ± 2.98 |
| A375 | skin | 1.87 ± 1.25 | 6.14 ± 1.45 | 12.07 ± 1.64 | 6.23 ± 1.96 | 3.06 ± 1.31 | 13.12 ± 3.58 |
| A431 | cervix | 1.46 ± 0.91 | 6.69 ± 3.27 | 7.14 ± 3.18 | 6.33 ± 1.99 | 3.03 ± 1.02 | 15.56 ± 2.85 |

| Cell line | Tissue type | $IC_{50}$ (μM) ± S.D. Compound[b] | | | |
|---|---|---|---|---|---|
| | | 7 | 8 | CDDP | OXP |
| HCT-15 | colon | 72.12 ± 4.74 | 13.69 ± 3.81 | 15.53 ± 2.48 | 1.25 ± 1.05 |
| SW480 | colon | 69.41 ± 11.51 | 10.58 ± 2.01 | 7.67 ± 1.34 | 4.20 ± 0.75 |
| CaCo-2 | colon | 97.28 ± 4.82 | 18.77 ± 2.81 | 18.31 ± 2.21 | 1.02 ± 0.25 |
| DLD-1 | colon | 82.24 ± 5.54 | 8.26 ± 3.24 | 8.01 ± 2.22 | 5.81 ± 1.93 |
| MCF-7 | breast | 112.1 ± 9.52 | 12.56 ± 2.47 | 8.37 ± 2.96 | 3.36 ± 1.69 |
| A375 | skin | 75.14 ± 6.54 | 4.99 ± 1.15 | 2.06 ± 1.01 | 2.37 ± 1.31 |
| A431 | cervix | 59.53 ± 3.64 | 7.41 ± 2.11 | 1.96 ± 0.84 | 3.69 ± 1.03 |

[a] Cells (3-8 × 10$^4$ m$^{-1}$) were treated for 72 h with increasing concentrations of the test compounds. Cytotoxicity was assessed by MTT test. $IC_{50}$ values were calculated by four parameter logistic model ($p < 0.05$). S.D. = standard deviation.
[b] 1: [$PtCl_2$(cis-1,4-DACH)]
2: [$PtCl_2$(1R,2R-DACH)]
3: [Pt(OXA)(cis-1,4-DACH)]
4: cis,trans,cis-[$Pt^{IV}Cl_2(OH)_2$(cis-1,4-DACH)]
5: cis,trans,cis-[$Pt^{IV}Cl_2(DCA)_2$(cis-1,4-DACH)]
6: [Pt(CBDCA)(cis-1,4-DACH)]
7: cis,trans,cis-[$Pt^{IV}$(OXA)(OH)$_2$(cis-1,4-DACH)]
8: cis,trans,cis-[$Pt^{IV}$(OXA)(DCA)$_2$(cis-1,4-DACH)]
CDDP: cisplatin
OXP: oxaliplatin Compound 1 was found, on average, slightly more effective than oxaliplatin, much more effective than cisplatin (by a factor of 3-6) in two out of the seven cell lines particularly in HCT-15 and CaCo-2 cells characterized for their scarce sensitivity to cisplatin, and, on the average, 2-4 times more active than compound 2, which has the same diamine of oxaliplatin but chloride leaving ligands like compound 1.

Compound 3 elicited an average cytotoxic activity lower than that of oxaliplatin and comparable to that of compound 2 and cisplatin, being, however, 3 times more effective than cisplatin against CaCo-2 colon cancer cells.

Compound 4 possessed an average cytotoxic potency lower than oxaliplatin but slightly higher than cisplatin, with $IC_{50}$ values in five out of the seven cell lines up to 2-fold lower than that of cisplatin.

Compound 5 was found to possess, on average, a cytotoxic activity rather similar to oxaliplatin and roughly 3 times better than cisplatin and compound 2.

Compounds 6 and 7 possessed a mean cytotoxic potency lower than oxaliplatin and cisplatin.

Compound 8 elicited an average cytotoxic activity lower than that of oxaliplatin and comparable to that of cisplatin.

The eight compounds were additionally tested for their in vitro antitumor activity in two pairs of human cell lines which were selected for their resistance to cisplatin (ovarian cancer cells 2008/C13*), or oxaliplatin (colon cancer cells LoVo/LoVo-OXP). A LoVo cell line retaining a multidrug resistance phenotype was also considered (LoVo MDR). Cross-resistance profiles were evaluated by means of the resistance factor (RF), which is defined as the ratio between the $IC_{50}$ value for the resistant cells and that arising from the sensitive cells (Table 2).

the case of colon cancer cells) towards the sensitive lines. Moreover, compound 1 does not show cross-resistance with cisplatin (RF 0.9), nor with oxaliplatin (RF 1.2). On the other hand, oxaliplatin is partially cross-resistant with cisplatin (RF 2.0) and cisplatin partially cross-resistant with oxaliplatin (RF 1.7). Compound 2, which has the same diamine as oxaliplatin but two leaving chlorides like cisplatin and compound

TABLE 2

Cross-resistance profiles[a]

| Compound[b] | $IC_{50}$ (μM) ± S.D. | | | | | | | |
|---|---|---|---|---|---|---|---|---|
| | 2008 | C13* | R.F. | LoVo | LoVo-OXP | R.F. | LoVo-MDR | R.F. |
| 1 | 1.89 ± 1.04 | 1.77 ± 0.92 | 0.9 | 1.11 ± 0.45 | 1.29 ± 0.82 | 1.2 | 1.09 ± 0.46 | 1.2 |
| 2 | 8.57 ± 2.03 | 17.06 ± 1.35 | 2 | 5.62 ± 0.94 | 14.64 ± 1.84 | 2.6 | 5.07 ± 0.82 | 2.6 |
| 3 | 11.13 ± 2.98 | 15.63 ± 3.06 | 1.4 | 7.02 ± 0.56 | 12.53 ± 1.92 | 1.8 | 10.33 ± 2.73 | 1.5 |
| 4 | 9.42 ± 1.16 | 13.85 ± 3.53 | 1.5 | 6.64 ± 2.70 | 9.46 ± 2.15 | 1.6 | 9.26 ± 2.11 | 1.5 |
| 5 | 2.15 ± 0.95 | 3.35 ± 0.85 | 1.6 | 2.27 ± 1.31 | 3.23 ± 1.08 | 1.4 | 3.26 ± 1.13 | 1.5 |
| 6 | 27.23 ± 2.09 | 52.25 ± 4.21 | 1.9 | 29.32 ± 3.52 | 56.20 ± 4.41 | 1.9 | 42.23 ± 3.31 | 1.4 |
| 7 | 59.53 ± 3.64 | 78.72 ± 4.60 | 1.3 | 61.25 ± 5.51 | 66.88 ± 5.12 | 1.1 | 69.42 ± 4.83 | 1.1 |
| 8 | 11.12 ± 3.28 | 9.12 ± 2.79 | 0.8 | 9.08 ± 2.16 | 11.14 ± 3.05 | 1.2 | 11.86 ± 3.33 | 1.3 |
| OXP | 1.65 ± 1.01 | 3.33 ± 1.84 | 2 | 1.02 ± 0.56 | 17.50 ± 1.79 | 17 | 1.36 ± 0.81 | 1.3 |
| CDDP | 2.26 ± 1.06 | 23.73 ± 2.42 | 10.5 | 7.63 ± 1.53 | 13.13 ± 2.47 | 1.7 | 7.53 ± 0.98 | 1.1 |

[a]Cells (3-8 × 10$^4$ mL$^{-1}$) were treated for 72 h with increasing concentrations of tested compounds. Cytotoxicity was assessed by MTT test. $IC_{50}$ values were calculated by four parameter logistic model (p < 0.05). S.D. = standard deviation. Resistant Factor (RF) is defined as $IC_{50}$ resistant/parent line.
[b]1: [PtCl$_2$(cis-1,4-DACH)]
2: [PtCl$_2$(1R,2R-DACH)]
3: [Pt(OXA)(cis-1,4-DACH)]
4: cis,trans,cis-[Pt$^{IV}$Cl$_2$(OH)$_2$(cis-1,4-DACH)]
5: cis,trans,cis-[Pt$^{IV}$Cl$_2$(DCA)$_2$(cis-1,4-DACH)]
6: [Pt(CBDCA)(cis-1,4-DACH)]
7: cis,trans,cis-[Pt$^{IV}$(OXA)(OH)$_2$(cis-1,4-DACH)]
8: cis,trans,cis-[Pt$^{IV}$(OXA)(DCA)$_2$(cis-1,4-DACH)]
CDDP: cisplatin
OXP: oxaliplatin Cisplatin resistance is multifactorial in nature, however the main molecular mechanisms involved in drug resistance of C13* cancer cells have been identified in high cellular glutathione and thioredoxin reductase levels, in reduced cellular drug uptake, and in enhanced repair of DNA damage. The molecular mechanisms involved in oxaliplatin resistance have not been so well characterized, however they appear to be: i) decreased cellular accumulation, which is thought to be related to a greater activity of the ATP7B exporter rather than to the activity of P-glycoprotein (P-gp) and multidrug resistance protein 1 (MRP1), and ii) more efficient repair of oxaliplatin induced DNA damage by NER (Nucleotide Excision Repair) (Zhou, Y., et al., *World J. Gastroenterol.*, 2010, 16, 2291-2297; Kamazawa, S., et al., *Gynecol. Oncol.*, 2002, 86, 171-176; Zhang, Y. H., et al., *Cancer Lett.*, 2010, 291, 76-82; and Noordhuis, P., et al., *Biochem. Pharmacol.* 2008, 76, 53-61).

It is noteworthy that, although oxaliplatin induces the same type of DNA crosslinks as cisplatin, it is effective also in cell lines resistant to cisplatin, thus suggesting that the two complexes may have different mechanism of resistance (Gatti, L.; Perego, P. Cellular resistance to oxaliplatin and drug accumulation defects. In: Bonetti, A. et al., editors. Cancer drug discovery and development platinum and other heavy metal compounds in cancer chemotherapy. New York: Humana Press; 2009. p. 115-124).

LoVo-OXP cells (derived from LoVo cells grown in the presence of increased concentrations of oxaliplatin) were 17-fold more resistant than parental cells (see Table 2). The data reported in Table 2 clearly indicate that compound 1 is as good as oxaliplatin and better than cisplatin (particularly in 1, is, on the average, 5-10 times less effective than compound 1 and exhibits partial cross-resistance to both cisplatin (RF 2.0) and oxaliplatin (RF 2.6).

Compounds 3 and 4 were less effective than oxaliplatin and cisplatin towards ovarian sensitive cell line and rather similar to cisplatin against LoVo colon cancer cells. However, compounds 3 and 4 did show cross-resistance with ciplatin (RF 1.4 and 1.5, respectively), but were only partially cross-resistant with oxaliplatin (RF 1.8 and 1.6, respectively).

Compound 5 was found to possess a cytotoxic activity better than cisplatin and similar to oxaliplatin against sensitive cells, showing no cross-resistance with both oxaliplatin (RF 1.4) and cislatin (RF 1.6).

Compound 6 was less effective than oxaliplatin and cisplatin towards both ovarian and colon cancer cells. However, compounds 6 was only partially cross-resistant with oxaliplatin and cisplatin (RFs 1.9).

Compound 7 was less effective than oxaliplatin and cisplatin towards both ovarian and colon cancer cells. However, it was able to overcome both cisplatin (RFs 1.3) and oxaliplatin resistances (RF 1.1).

Compound 8 was found to possess a cytotoxic activity lower than cisplatin and oxaliplatin in ovarian sensitive cancer cells, similar than cisplatin against colon sensitive cells, and showing no cross-resistance with both oxaliplatin (RF 0.8) and cisplatin (RF 1.2).

These findings are in agreement with those previously reported for human ovarian 2780/2870R cancer cells, (Kasparkova, J., et al., *Biochem. Pharmacol.* 2010, 79, 552-564) and for murine leukemia [PtCl$_2$(1,2-DACH)]-resistant cells (Hoeschele, J. D., et al., *J. Med. Chem.* 1994, 37, 2630-2636).

Therefore, it is possible to conclude that in human colorectal cancer cells compounds 1, 3, 4 and 5 are not recognized as a Pt(DACH) complex confirming that differences in shape of the diamine ligand can play a key role in the antitumor effect of Pt(DACH) complexes.

In Table 2 are also reported the results obtained in a multidrug resistant (MDR) colon carcinoma subline, LoVo MDR, in which the resistance to doxorubicin, a drug belonging to the MDR spectrum, is associated with an overexpression of multi-specific drug transporters, such as the 170 kDa P-glycoprotein (P-gp) (Wersinger, C., et al., *Amino Acids* 2000, 19, 667-685). It is well known that acquired MDR, whereby cells become refractory to multiple drugs, poses most important challenge to the success of anticancer chemotherapy. Although cisplatin is not a P-glycoprotein substrate, many multidrug resistance proteins (MRP1, MRP2, MRP4) have been claimed to be involved in platinum complex transport and be responsible for its afflux to/efflux from the cell (Zhou, Y., et al., *World J. Gastroenterol.*, 2010, 16, 2291-2297; Kamazawa, S., et al., *Gynecol. Oncol.*, 2002, 86, 171-176; and Zhang, Y. H., et al., *Cancer Lett.*, 2010, 291, 76-82).

All platinum derivatives tested against this cell line showed a similar response as for the parental subline, thus suggesting that platinum drugs are not P-gp substrates.

4. Cellular Uptake

LoVo and LoVo-OXP cells ($2\times10^6$) were seeded in 75 cm$^2$ flasks in growth medium (20 ml). After 24 h, the medium was replaced and the cells incubated for different times (6, 24 or 48 h) in the presence of the tested complexes. Cell monolayers were washed twice with cold PBS and harvested. Samples were subjected to three freezing/thawing cycles at −80° C., and then vigorously vortexed. Aliquots were removed for the determination of protein content by the BioRad protein assay (BioRad). The samples were treated with 1 mL of highly pure nitric acid (Pt: ≤0.01 µg×kg$^{-1}$, TraceSELECT® Ultra, Sigma Chemical Co.) and transferred into a microwave teflon vessel. Subsequently, samples were submitted to a standard procedure using a speed wave MWS-3 Berghof instrument (Eningen, Germany). After cooling, each mineralized sample was analyzed for platinum by using a Varian AA Duo graphite furnace atomic absorption spectrometer (Varian, Palo Alto, Calif.; USA) at the wavelength of 324.7 nm. The calibration curve was obtained using known concentrations of standard solutions purchased from Sigma Chemical Co.

5. Cellular Uptake and Lipophilicity

It is well-known that cellular uptake is an important factor influencing drug efficacy. Moreover, since one of the main mechanisms controlling oxaliplatin resistance is cellular uptake, uptake experiments were performed in human colorectal cancer cells sensitive and resistant to oxaliplatin. Cancer cells were treated for 6, 24, and 48 h with 5 µM concentrations of compounds 1, 2, and oxaliplatin. The intracellular platinum was quantified by means of GF-AAS analysis and the results, expressed as µg metal mg$^{-1}$ of cellular proteins, are summarized in FIG. 2.

Figure 2:
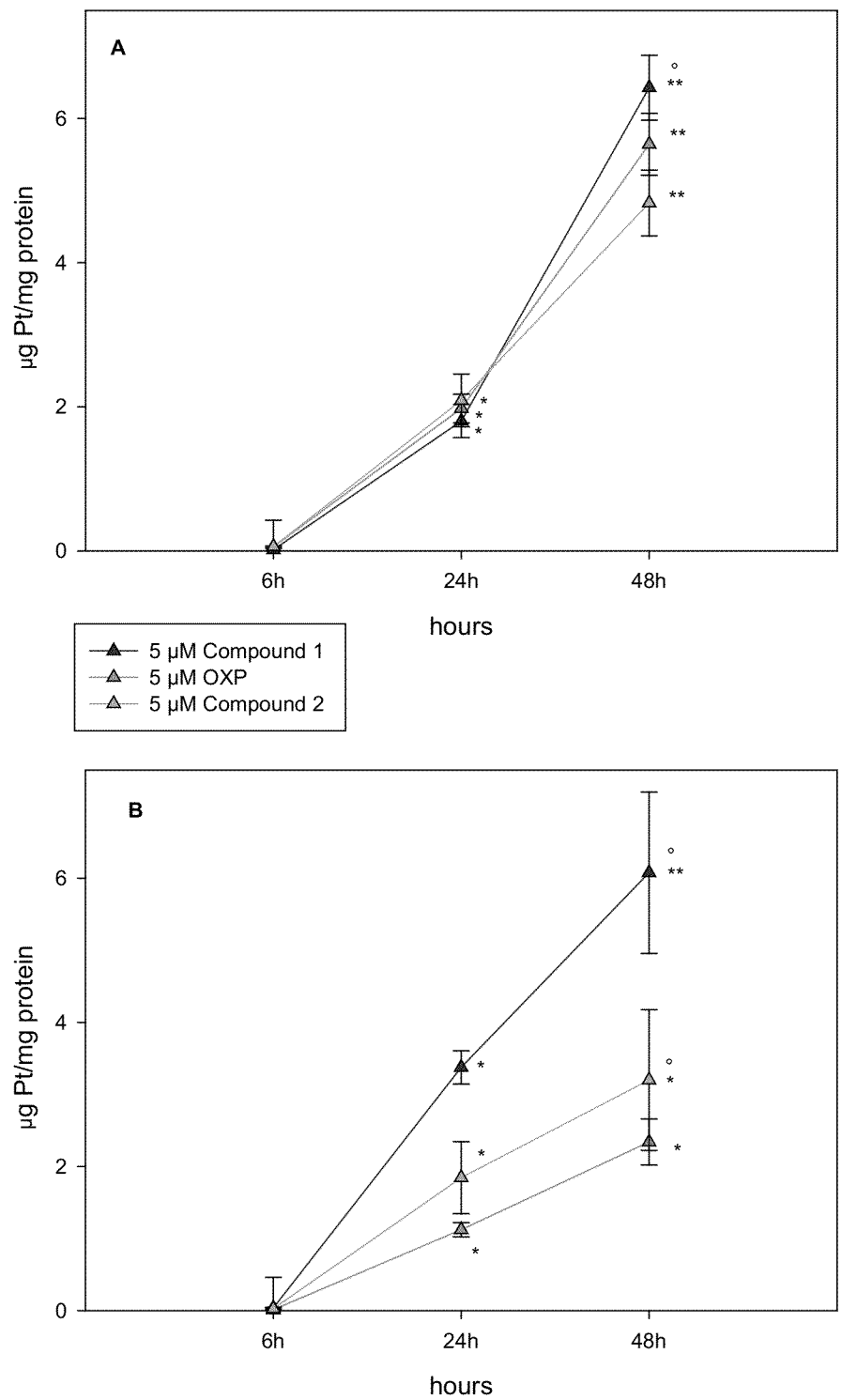
FIG. 2: Intracellular accumulation of platinum complexes detected by GF-AAS analysis. LoVo (panel A) and LoVo-OXP (panel B) cells were incubated with 5 µM of compound 1, compound 2, and oxaliplatin (OXP) for 6, 24, and 48 h. Error bars indicate standard deviation. *$p<0.05$ and **$p<0.01$ compared to control, °$p<0.05$ compared to oxaliplatin treated cells.

The platinum cellular uptake was time dependent for all platinum complexes and for sensitive as well as for resistant LoVo cells (FIG. 2). There is, however, a marked difference between sensitive and resistant cells as far as the discrimination between different complexes is concerned. In LoVo sensitive cells (FIG. 2, panel A) the amount of incorporated drug is practically the same for the three types of complexes, clearly indicating that the smaller activity of compound 2 in this colon tumor cell line is to be ascribed to factors other than cellular drug uptake. In resistant LoVo-OXP cells (FIG. 2, panel B) the cellular uptake is remarkably decreased for oxaliplatin and compound 2 (both compounds having the 1,2-DACH ligand) but not for compound 1 which is internalized with the same efficacy in LoVo as well as in LoVo-OXP cells. These data can well explain the lack of cross-resistance between compound 1 and oxaliplatin. It is also to be noted that while for compound 2 the observed RF (2.6) can be accounted for by the reduced cellular uptake, in the case of oxaliplatin the observed RF (17.0) is far too great to be justified only on the basis of differential cellular uptake.

The main differences between cisplatin and oxaliplatin are distribution in the body, cellular accumulation, and recognition and processing of DNA adducts. These differences are ascribable, at least in part, to the presence of the organic diamine ligand in oxaliplatin, which confers lipophilicity and steric bulk. On this basis, other groups have pursued the preparation of platinum derivatives having methyl-substituted 1R,2R-DACH ligand with the aim of improving the cytotoxic and anticancer properties of the drug by increasing its lipophilicity and steric bulk (Abramkin, S. A., et al., *J. Med. Chem.* 2010, 53, 7356-7364). It is generally found that the cellular uptake of platinum complexes correlates with their lipophilicities (Platts, J. A., et al, *J. Med. Chem.* 2001, 44, 472-474 and Ghezzi, A. R., et al., *J. Inorg. Biochem.* 2004, 98, 73-78).

Lipophilicity is usually expressed in terms of n-octanol/water partition coefficient, log $P_{o/w}$, and correlates with cellular uptake by passive diffusion (Liu, X., et al., *Pharm. Res.* 2011, 28, 962-977).

Since RP-HPLC retention is due to partitioning between mobile (polar) and stationary (apolar) phases, there is a good correlation between capacity factor k' ($k'=(t_R-t_0)/t_0$, where $t_0$ is the retention time for an unretained compound and $t_R$ is the retention time of the analyte) and partition coefficient (log $P_{o/w}$=a+b log k'). Thus the HPLC procedure represents a good alternative to the time- and material-consuming shake-flask method. By using the HPLC procedure, log $P_{o/w}$ of compound 1 was found to be −1.57±0.10 (Margiotta, N., et al., *J. Med. Chem.* 2012, 55(16), pp 7182-7192), in good agreement with that of compound 2 (log $P_{o/w}$=−1.40) or oxaliplatin (log $P_{o/w}$=−1.39) (Platts, J. A., et al., *J. Inorg. Biochem.* 2006, 100, 1199-1207) but significantly greater than that of cisplatin (log $P_{o/w}$=−2.27) or [PtCl$_2$(en)] (log $P_{o/w}$=−2.16; en=ethylenediamine). Thus, the intracellular platinum accumulation exhibited by compounds 1, 2, and oxaliplatin in sensitive LoVo cells (FIG. 2 panel A) appears to be strictly related to their very similar log $P_{o/w}$, which could imply that the three complexes enter the cells by a similar route and this could be (but not exclusively be) passive diffusion. On the contrary, in the case of oxaliplatin-resistant LoVo-OXP cells, the cellular accumulation decreases remarkably for compound 2 and oxaliplatin (containing 1,2-DACH ligand) but not for compound 1 (containing cis-1,4-DACH). This implies that there are specific import (CTR1, OCT, etc.) or export (ATP7B) mechanisms which operate selectively on the different types of complexes.

B. In Vivo Assays

1. In Vivo Anticancer Activity Toward Lewis Lung Carcinoma

All studies involving animal testing were carried out in accordance with the ethical guidelines for animal research adopted by the University of Padua, acknowledging the Italian regulation and the European Directive 86/609/EEC as to animal welfare and protection and the related codes of practice. The mice were purchased from Charles River, Italy, and housed in steel cages under controlled environmental conditions (constant temperature, humidity, and 12 h dark/light cycle) and alimented with commercial standard feed and tap water ad libitum. Animals were observed daily, and body weight and food intake recorded. The Lewis lung carcinoma (LLC) cell line was purchased from ECACC, UK. The LLC cell line was maintained in D-MEM (Euroclone) supplemented with 10% heat-inactivated FBS (Euroclone), 10 mM L-glutamine, 100 U mL$^{-1}$ penicillin, and 100 μg mL$^{-1}$ streptomycin in a 5% CO$_2$ air incubator at 37° C.

The Lewis lung carcinoma (LLC) was implanted i.m. as a 2×10$^6$ cell inoculum into the right hind leg of 8-week old male and female C57BL mice (24±3 g body weight). After 24 h from tumor implantation, mice were randomly divided into five groups (8 animals per group, 10 controls) and treated with a daily i.p. injection of compound 1 (1.5 and 3 mg kg$^{-1}$ in 0.9% NaCl solution), cisplatin (1.5 mg kg$^{-1}$ in 0.9% NaCl solution), or the vehicle solution (0.9% NaCl solution) from day 9 after tumor inoculation (palpable tumor). At day 15, animals were sacrificed, the legs were amputated at the proximal end of the femur, and the inhibition of tumor growth was determined according to the difference in weight of the tumor-bearing leg and the healthy leg of the animals expressed as % referred to the control animals. Body weight was measured every two days and was taken as a parameter for systemic toxicity.

All the values are the means±S.D. of not less than three measurements. Multiple comparisons were made by Tukey-Kramer test (**p<0.01; *p or °p<0.05).

2. In Vivo Antitumor Activity in Lewis Lung Carcinoma (LLC)

Figure 3:
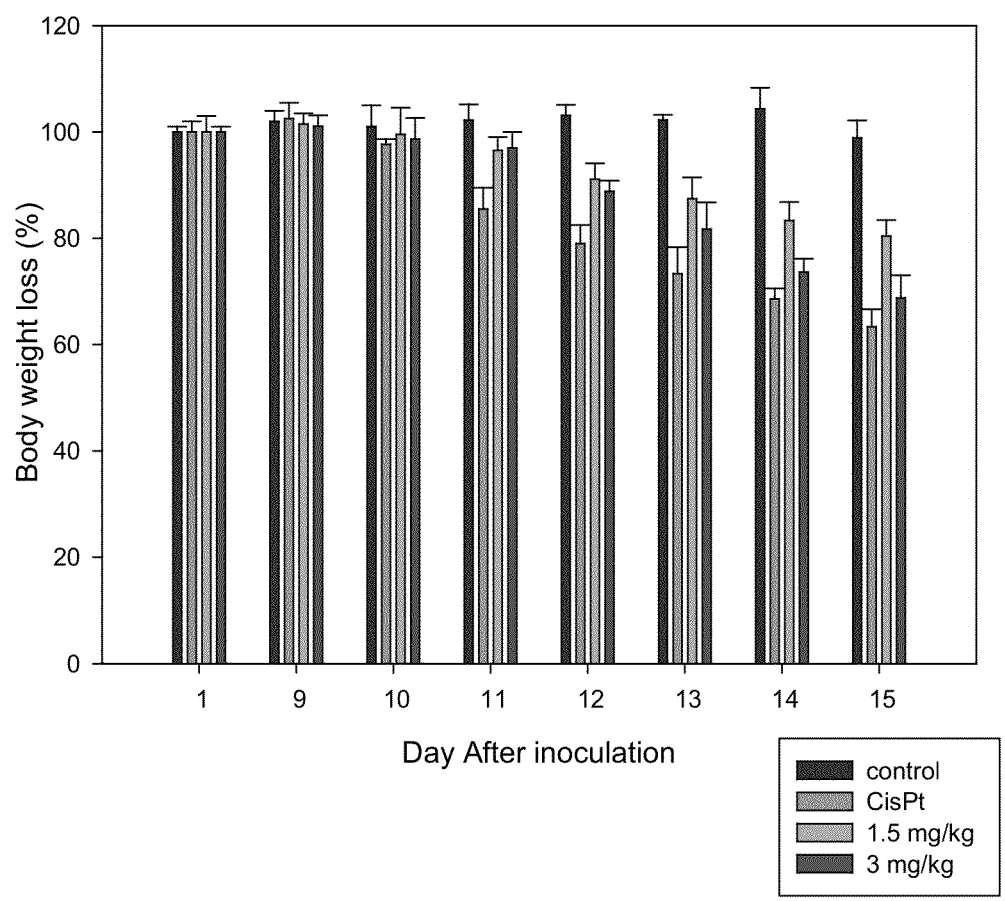
FIG. 3: The body weight changes of LLC-bearing C57BL mice treated with vehicle or tested compounds. Each drug was administered daily from day 9 and the weights were detected at day 1 and daily from day 9. The error bars indicate the S.D.

The in vivo antitumor activity of compound 1 was evaluated in a model of solid tumor, the syngeneic murine Lewis lung carcinoma (LLC). Tumor growth inhibition induced by compound 1 was compared with that promoted by the reference metallodrug cisplatin. From day 9 after tumor inoculation, when tumors became palpable, tumor-bearing mice received daily doses of compound 1 (1.5 and 3 mg kg$^{-1}$) or cisplatin (1.5 mg kg$^{-1}$). Tumor growth was estimated at day 15, and the results are summarized in Table 3. For the assessment of the adverse side effects, changes in body weights of tumor-bearing mice were monitored daily (FIG. 3).

Compound 1 is better tolerated than cisplatin and could be administered also at a greater dose (3 mg kg$^{-1}$). The inhibition of tumor cell proliferation for the three compounds is shown in Table 3.

TABLE 3

In vivo anticancer activity toward murine Lewis lung carcinoma (LLC). Starting from day 9 after tumor implantation, tested compounds were daily administered i.p. At day 15, mice were sacrificed and tumor growth was detected as described above. Tukey-Kramer test **p < 0.01.

|  | Daily dose i.p. (mg kg$^{-1}$) | Average tumor weight (mean ± SD, g) | Inhibition of tumor growth (%) |
| --- | --- | --- | --- |
| Control$^a$ | — | 0.778 ± 0.05 | — |
| 1 | 1.5 | 0.253 ± 0.09** | 67.48 |
| 1 | 3 | 0.158 ± 0.06** | 79.69 |
| cisplatin | 1.5 | 0.199 ± 0.10** | 74.66 |

$^a$Vehicle (0.9% NaCl).

Even at the lower daily dose of 1.5 mg kg$^{-1}$, compound 1 exerts a statistically significant (p<0.01) antitumor activity, with a tumor growth inhibition of 67%. A reduction (about 80%) of the tumor volume was achieved using a daily dose of 3.0 mg kg$^{-1}$. The antitumor activity of cisplatin (75%) is in between those obtained with compound 1 at the two different doses. It is however remarkable that the body weight loss (depicted in FIG. 3) indicates that, even at the higher dose (3 mg kg$^{-1}$), compound 1 had smaller adverse side effects than cisplatin and that, at equimolar dose (1.5 mg kg$^{-1}$), the weight loss caused by compound 1 is about half that caused by cisplatin.

3. In Vivo Anticancer Activity Toward Colorectal Oxaliplatin-Sensitive and -Resistant Xenograft Models LoVo and LoVo-OXP tumor xenografts were established in 6-week-old BALB/c nu/nu mice by injecting 1×10$^7$ tumor cells subcutaneously (100 μL in serum free medium) on the left dorsal flank. After 24 h from tumor implantation, mice were randomly divided into five groups (6 animals per group, 8 controls). Chemotherapy was delayed until the tumor became palpable (day 14). From day 14, 1 was dosed daily at 3 mg/kg ip whereas OXP was dosed daily at 2 mg/kg ip. Measurements of body weights and tumor volumes were recorded every 2 days until the experimental endpoint. The long axis (L) and the short axis (S) were measured with caliper, and the tumor volume (V) was calculated using the following equation: V=S×S×L/2. At day 30, animals were sacrificed, and the inhibition of tumor growth was determined by comparing the volume of the control group and the treatment group expressed as % referred to the control animals.

All the values are the means±S.D. of not less than three measurements. Multiple comparisons were made by Tukey-Kramer test (**p<0.01; *p<0.05).

4. In Vivo Activity Toward LoVo and LoVo-OXP Tumor Xenografts

Figure 4:
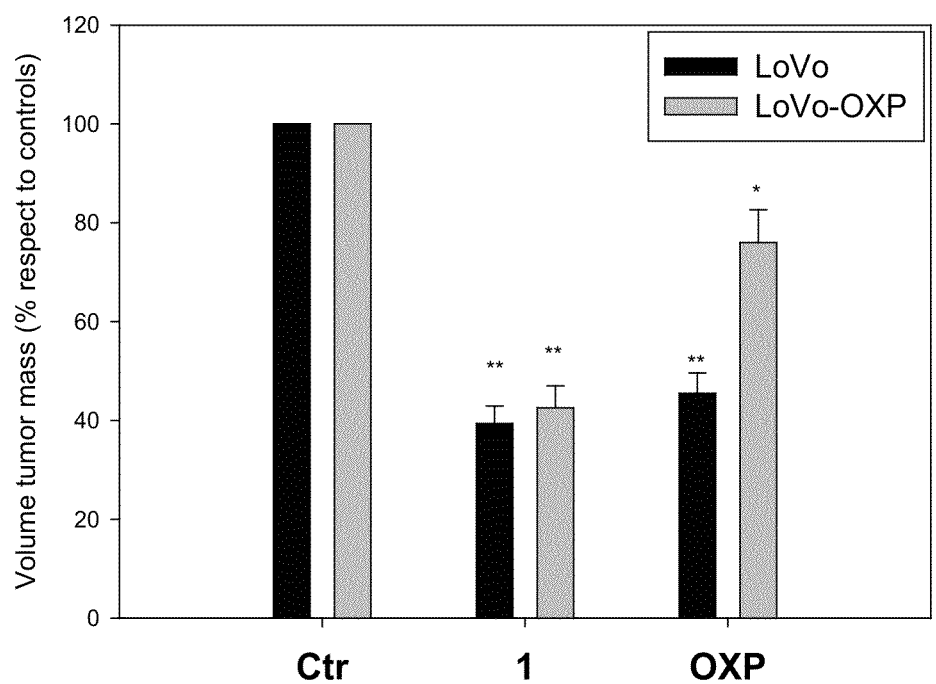
FIG. 4: In vivo anticancer activity against LoVo and LoVo-OXP xenograft models. BALB/C nude mice bearing established human LoVo and LoVo OXP colorectal adenocarcinoma xenografts were daily ip dosed with either vehicle (Ctr) 0.9% NaCl, 1 at 3 mg/kg or OXP at 2 mg/kg from day 14 to day 30. The error bars indicate the SD.
Figure 5:
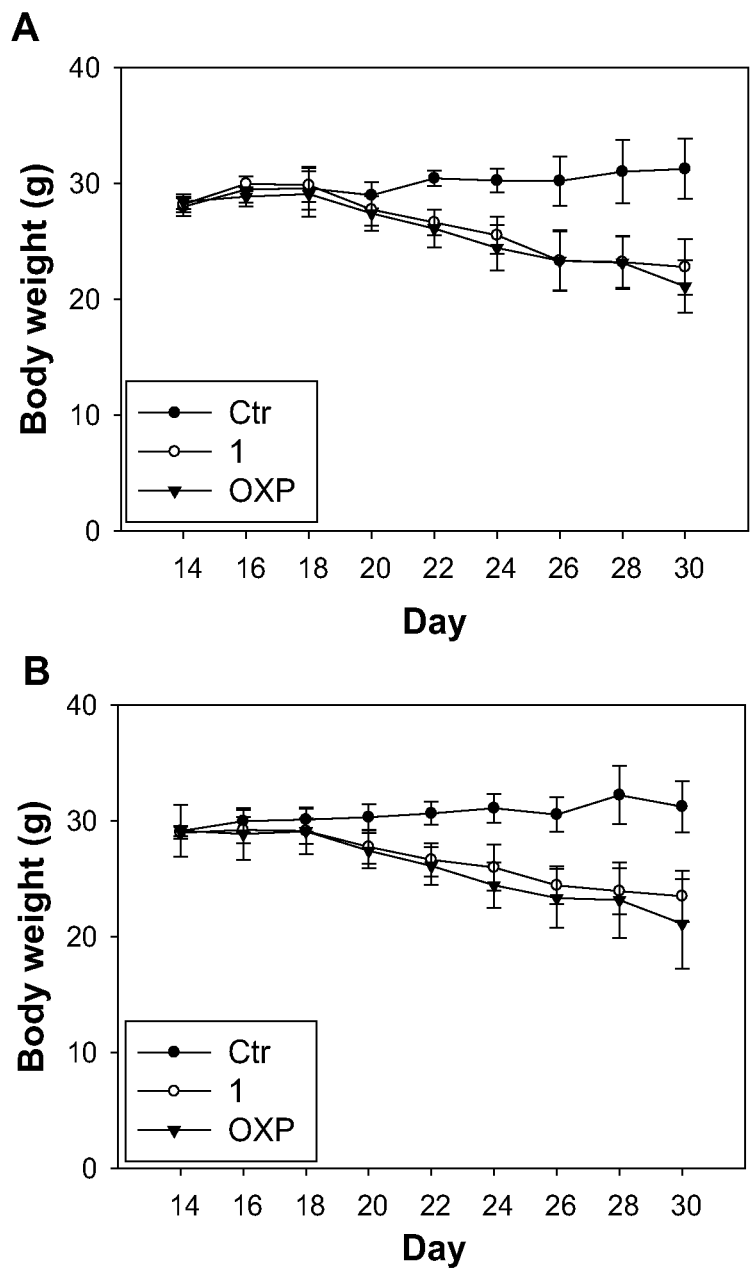
FIG. 5: Body weight changes. The body weight changes of LoVo (panel A) and LoVo-OXP (panel B) xenograft mice treated with vehicle (Ctr) or tested compounds. Body weight was daily measured, from day 14 to day 30, and was taken as a parameter of systemic toxicity. The error bars indicate the SD.

Compound 1 exerts a significant antitumor activity (FIG. 4) against both on LoVo and LoVo-OXP colorectal adenocarcinoma xenografts, with a tumor growth inhibition of 61% and 58% in LoVo and LoVo-OXP models, respectively. Conversely, the antitumor activity of oxaliplatin is comparable to that exerted by 1 against LoVo xenografts (tumor growth inhibition of 54%) but 2.4 times lower against LoVo-OXP models (tumor growth inhibition of 24%). Notably, the body weight loss (depicted in FIG. 5) induced by 1 was roughly equivalent to that obtained by using the parent drug oxaliplatin.

These in vivo data confirm the effectiveness of 1 in circumventing oxaliplatin resistance in LoVo-OXP colorectal adenocarcinoma models.

The unique antitumor effects of compound 1, coupled with its enhanced aqueous solubility compared to compound 2, make this compound a valuable agent against oxaliplatin-resistant colorectal cancer cells.

In summary, the in vitro and in vivo results for compounds of the present invention and particularly compound 1 show exceptional and unexpected activity against oxaliplatin refractory tumors. Compound 1 structurally differs from oxaliplatin only in the different bridging mode of the DACH carrier ligand, which creates a 7 membered ring in the case of 1,4-DACH and a 5 membered ring in the case of 1,2-DACH. The in vitro data demonstrated that this bite dissimilarity did not confer significant differences in terms of DNA binding mode between compound 1 and oxaliplatin. As it is well recognized that in cancer cells the main molecular mechanisms accounting for oxaliplatin resistance are related to DNA damage, the present results are even more surprising and unexpected. In spite of the fact that compound 1 interacts with DNA in a similar manner to oxaliplatin, it retains an unexpected ability in overcoming oxaliplatin resistance in colon cancer cells. At the present time, oxaliplatin resistance remains a major clinical challenge in combination chemotherapy treatment based on platinum drugs. Presently, apart from oxaliplatin, there are no other drugs in advanced clinical development which appear to be active against colorectal cancer and that may be used for the treatment of patients with oxaliplatin-refractory colorectal cancer. Based on the in vitro and in vivo data the compounds of the present invention and in particular the data for compound 1 fulfill a current pressing need for new antitumor agents for the treatment of oxaliplatin resistant colon cancer.

The following nonlimiting examples illustrate the inventors' preferred methods for preparing the compounds of the invention.

Materials and Methods:

$^1$H 1D and 2D NMR spectra were recorded on Bruker Avance DPX 300, Bruker Avance II 600 MHz, and Bruker Avance III 700 MHz instruments. $^{195}$Pt NMR spectra were recorded on a Bruker Avance DPX 300 MHz instrument. $^1$H chemical shifts were referenced using the internal residual protic peak of the solvent (2.50 ppm for DMSO-$d_6$, 8.03 ppm for DMF-$d_7$, 4.8 ppm for $D_2O$). $^{195}$Pt NMR spectra were referenced relative to $K_2PtCl_4$ (external standard placed at −1620 ppm with respect to $Na_2[PtCl_6]$). ESI-MS spectra were recorded on Agilent 1100 Series LC-MSD-Trap-System VL. IR spectra were obtained on a Perkin-Elmer IR Fourier transform spectrophotometer in KBr pellets. Elemental analyses were carried out with a Hewlett Packard 185 C, H, and N analyzer.

Example 1

Compound 1, [SP-4-2-(cis)]-dichloro(1,4-cyclohexanediamine-N,N')platinum("[PtCl$_2$(cis-1,4-DACH)]")

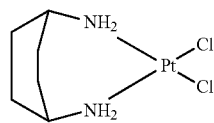

[PtCl$_2$(cis-1,4-DACH)], compound 1, was prepared according to the procedure described by Ranaldo, R., et al., *Inorg. Chem.* 2008, 47, 2820-2830.

Example 2

Compound 2, [SP-4-2]-dichloro[(1R,2R)-1,2-cyclohexanediamine-N$^1$,N$^2$]platinum("[PtCl$_2$(1R,2R-DACH)]")

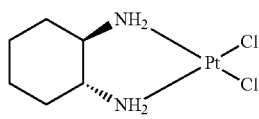

[PtCl$_2$(1R,2R-DACH)], compound 2, was prepared using the methodology described in Dhara, S. C., *Indian J. Chem.* 1970, 8, 193-194.

Briefly, $K_2[PtCl_4]$ (0.726 g, 1.75 mmol) was dissolved in a minimum amount of water (15 mL) and the resulting red solution was treated with KI (1.74 g, 10.5 mmol). After stirring for 5 min, the brown solution was treated with 1R,2R-diaminocyclohexane (200 mg, 1.75 mmol) which caused the immediate formation of a yellow precipitate. The suspension was stirred for 3 h. The yellow precipitate, [PtI$_2$(1R,2R-DACH)], was then collected by filtration, washed with water, ethanol, and diethylether, dried under vacuum, and analyzed by elemental analysis. A yield of 1.36 g (91%) was obtained. [PtI$_2$(1R,2R-DACH)] (182 mg, 0.32 mmol) was then suspended in 20 mL of water and treated with AgNO$_3$ (109 mg, 0.64 mmol) which caused the immediate formation of a yellow precipitate (AgI). The suspension was kept at 55° C. in the dark for 30 min, AgI was separated by filtration of the mother liquor through celite, and the filtrate was treated with KCl (1.43 g, 1.92 mmol). The resulting solution was stirred at 55° C. for 30 min, resulting in the formation of a yellow precipitate. The yellow precipitate, corresponding to compound 2, was isolated by filtration, washed with ice-cold water, ethanol, and ether and then dried under vacuum. A yield of 0.30 g (94%) was obtained.

The elemental analyses and the spectroscopic and spectrometric properties of the synthesized Pt-complexes were consistent with the data reported in the literature (Ranaldo, R., et al., *Inorg. Chem.* 2008, 47, 2820-2830 and Kidani, Y, et al., *J. Med. Chem.* 1978, 21, 1315-1318). The purity of synthesized compounds was higher than 95% as established by combustion analysis.

Example 3

Compound 3, [SP-4-2-(cis)]-(1,4,cyclohexanediamine-N,N')[ethanedioato(2)-O,O$^1$]platinum("[Pt(OXA)(cis-1,4-DACH)]" (OXA-oxalate, (COO—)$_2$)

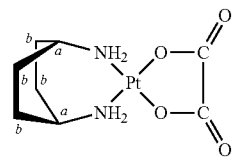

Oxalic acid [OXA, (COOH)$_2$, 0.041 g, 0.45 mmol] was dissolved in water (40 mL) and the resulting solution was treated in the dark with Ag$_2$O (0.104 g, 0.45 mmol) for 15 min at 50° C. The resulting suspension was added to [PtCl$_2$(cis-1,4-DACH)] (0.171 g, 0.45 mmol), stirred with a magnetic stirrer in the dark at 50° C. for 90 min and then at room temperature for 24 h. The white precipitate that formed (AgCl) was filtered thorough celite and the filtrate evaporated under vacuum at 40° C. The light yellow residue (0.134 g, 0.34 mmol; yield 75%) corresponds to [Pt(OXA)(cis-1,4-DACH)].

$^1$H NMR: (D$_2$O) 5.29 (4H, NH$_2$), 2.89 (2H, CHa, see Figure above for the numbering of protons), 3.21 (4H, CHa), 1.76 (8H, CHb) ppm. $^{195}$Pt NMR: (D$_2$O) -1865 ppm. ESI-MS: calculated for [C$_8$H$_{14}$N$_2$O$_4$PtNa]$^+$[3+Na]$^+$: 420.0. Found: $^m$/z 420.0. Anal.: calculated for $C_8H_{16}N_2O_5Pt$ (3.$H_2O$): C, 23.14; H, 3.88; N, 6.74%. Found: C, 23.44; H, 3.61; N, 6.73%.

Example 4

Compound 4, (OC-6-33)-dichloro(cis-1,4-cyclohexanediamine-N,N')dihydroxyplatinum("cis,trans,cis-[$Pt^{IV}Cl_2(OH)_2$(cis-1,4-DACH)]")

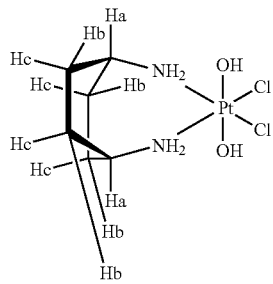

cis,trans,cis-[$PtCl_2(OH)_2$(cis-1,4-DACH)], compound 4, was prepared using a modified method according to Shamsuddin, S., et al., *J. Inorg. Biochem.*, 1998, 71, 29-35.

Briefly, a suspension of [$PtCl_2$(cis-1,4-DACH)] (compound 1) (208.6 mg, 0.55 mmol) in 28 mL of $H_2O$ was treated with a solution of $H_2O_2$ in $H_2O$ (30% w/w, 2.0 mL). The mixture was stirred in the dark at 70° C. for 2 h. The resulting yellow solution was filtered and then concentrated under reduced pressure to a minimum volume. Addition of acetone induced the formation of a pale yellow precipitate that was isolated by filtration of the mother liquor, washed with ice cold water, and dried under vacuum to afford 183 mg (0.44 mmol; 80% yield) of cis,trans,cis-[$PtCl_2(OH)_2$(cis-1,4-DACH)].

$^1$H NMR: (DMSO-$d_6$) 6.33 (4H, $NH_2$), 2.89 (2H, CHa, see Figure above for the numbering of protons), 2.07 (4H, CHbHc), 1.45 (4H, CHbHc) ppm; (DMF-$d_7$) 6.70 (4H, $NH_2$), 3.25 (2H, CHa), 2.26 (4H, CHbHc), 1.67 (4H, CHbHc) ppm. $^{195}$Pt NMR: (DMSO-$d_6$) 964.6 ppm; (DMF-$d_7$) 871.7 ppm. IR: (KBr pellet) 3421, 3210, 1629, 1574, 547, 396, 322, 215 cm$^{-1}$. ESI-MS: calculated for $C_6H_{16}N_2Cl_2O_2PtNa$ [4+Na]$^+$: 437.01. Found: $^m$/z 436.9. Anal.: calculated for $C_6H_{18}N_2Cl_2O_3Pt$ (4.$H_2O$): C, 16.67; H, 4.20; N, 6.48%. Found: C, 16.42; H, 4.15; N, 6.29%.

Example 5

Compound 5, (OC-6-33)-dichloro(cis-1,4-cyclohexanediamine-N,N')bisdichloroacetateplatinum ("cis,trans,cis-[$Pt^{IV}Cl_2(DCA)_2$(cis-1,4-DACH)]") (DCA=dichloroacetate, $CHCl_2COO$—)

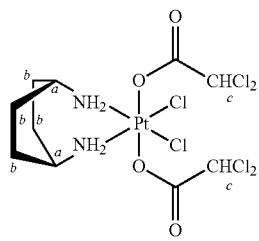

A suspension of cis,trans,cis-[$Pt^{IV}Cl_2(OH)_2$(cis-1,4-DACH)], compound 4, (example 4, 43 mg, 0.104 mmol) in THF (2 mL) was treated with dichloroacetic anhydride 125 mL. The mixture was stirred using a magnetic stirrer in the dark at room temperature for 17 h. The resulting yellow solution was treated with n-pentane until precipitation of a light yellow solid, which was isolated by filtration, washed with n-pentane and then with ice-cold water and finally dried under vacuum to afford 441 mg (62% yield) of cis,trans,cis-[$Pt^{IV}Cl_2(DCA)_2$(cis-1,4-DACH)].

$^1$H-NMR (DMSO-$d_6$): 7.92 (4H, $NH_2$), 6.58 (2H, CHc), 3.03 (2H, CHa), 1.63 (8H, CHb) ppm. $^{195}$Pt NMR (DMSO-$d_6$): 1195 ppm. ESI-MS: calculated for [$C_{10}H_{16}N_2Cl_6O_4PtNa$]$^{+[}$5+Na]$^+$: 659.0. Found: $^m$/z 658.7. Anal.: calculated for $C_{10}H_{16}N_2Cl_6O_4Pt$ (5): C, 18.88; H, 2.54; N, 4.40%. Found: C, 18.76; H, 2.58; N, 4.35%.

Example 6

Compound 6, [SP-4-2-(cis)]-(1,4-cyclohexanediamine-N,N')[cyclobutane-1,1-dicarboxylate-O,O'] platinum ("[Pt(CBDCA)(cis-1,4-DACH)]")

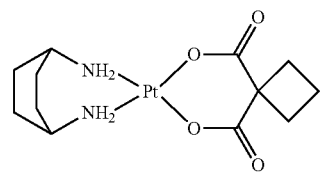

[Pt(CBDCA)(cis-1,4-DACH)], compound 6, was prepared according to the procedure described by Ranaldo, R., et al., *Inorg. Chem.* 2008, 47, 2820-2830.

Example 7

Compound 7, (OC-6-33)-[ethanedioato(2)-O,O'](cis-1,4-cyclohexanediamine-N,N')dihydroxyplatinum ("cis,trans,cis-[$Pt^{IV}$(OXA)(OH)$_2$(cis-1,4-DACH)]") (OXA=oxalate)

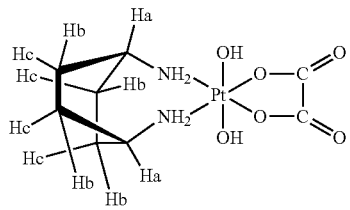

A solution of [Pt(OXA)(cis-1,4-DACH)] (170 mg, 0.428 mmol; this compound was prepared using the methodology described in S. Shamsuddin, I. Takahashi, Z. H. Siddik, A. R. Khokhar. J. *Inorg. Biochem.* 1996, 61, 291-301) in 17 mL of $H_2O$ was treated with a 855 µL of a solution of $H_2O_2$ in $H_2O$ (30% w/w). The mixture was stirred at room temperature for 24 h in the dark. The resulting suspension was concentrated under reduced pressure to a minimum volume. Addition of acetone induced the formation of a white precipitate that was isolated by filtration of the mother liquor, washed with acetone, and dried under vacuum. Yield 83% (151 mg, 0.35 mmol).

Anal.: calculated for $C_8H_{16}N_2O_6Pt$.0.5$H_2O$ (cis,trans,cis-[Pt(OXA)(OH)$_2$(cis-1,4-DACH)].0.5$H_2O$) C, 21.82; H, 3.89; N, 6.36%. Found: C, 21.83; H, 3.94; N, 6.13%.

ESI-MS: calculated for $C_8H_{16}N_2O_6PtK$ [7+K]$^+$ 470.39. Found: $^m/z$ 470.03.

$^1$H-NMR (DMSO-d$_6$): 6.71 (4H, NH$_2$), 2.91 (2H, CHa), 1.97 (2H, CHb), 1.50 (8H, CHc), 0.77 (2H, OH) ppm.

Example 8

Compound 8, (OC-6-33)-[ethanedioato(2)-O,O'](cis-1,4-cyclohexanediamine-N,N')bisdichloroacetate-platinum ("cis,trans,cis-[Pt$^{IV}$(OXA)(DCA)$_2$(cis-1,4-DACH)]") (OXA=oxalate; DCA=dichloroacetate, CHCl$_2$COO—)

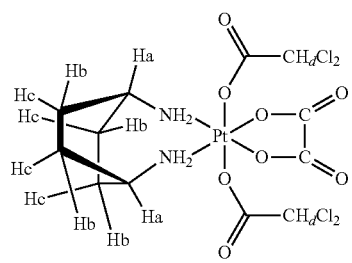

Dichloroacetic anhydride (282.5 μL, 1.85 mmol) was added to a suspension of cis,trans,cis-[Pt(OXA)(OH)$_2$(cis-1,4-DACH)] (compound 7) (100 mg, 0.232 mmol) in 7 mL of THF. The reaction mixture was stirred in the dark at room temperature for 17 h. The resulting white precipitate was isolated by filtration, washed with n-pentane and dried under vacuum. Yield 75.6% (117.3 mg, 0.18 mmol).

Anal.: calculated for $C_{12}H_{16}Cl_4N_2O_8Pt$ (cis,trans,cis-[Pt(OXA)(DCA)$_2$(cis-1,4-DACH)]) C, 22.07; H, 2.47; N, 4.29%. Found: C, 22.46; H, 2.73; N, 4.44%.

ESI-MS: calculated for $C_{12}H_{15}Cl_4N_2O_8Pt$ [8-H]$^-$ 650.92 Found: $^m/z$ 650.93.

$^1$H-NMR (DMSO-d$_6$): 7.69 (4H, NH$_2$), 6.53 (2H, CHd), 2.98 (2H, CHa), 1.72 (8H, CHb/c) ppm.

All publications including but not limited to journal articles, books, patents, patent applications, etc. described in this application are each herein incorporated by reference in their entirety.

Although the invention has been described herein with reference to the disclosed embodiments, persons skilled in the art will appreciate that the specific procedures, experiments, etc. detailed are illustrative of the invention. It should be understood that various modifications can be made without departing from the spirit of the invention. Therefore, the invention is limited only by the following claims.

We claim:

1. A method of treating refractory colorectal cancer in a mammal in need of such treatment comprising administering to said mammal a therapeutically effective amount of a compound of formula I

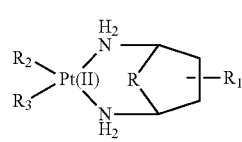

Formula I wherein R is —(CH$_2$)$_n$— in which n is an integer from one to three;

$R_1$ is hydrogen, carboxyl, an alkyl group of from one to four carbon atoms, an alkyl group of from one to four carbon atoms substituted with an alkoxy group of from one to four carbon atoms, a cycloalkyl group of from three to six carbon atoms, a hydroxyalkyl group of from one to four carbon atoms, an alkoxy group of from one to four carbon atoms or benzyl; and $R_2$ and $R_3$ are negatively charged monodentate ligands which may be the same or different and are selected from the group consisting of chloro, bromo, iodo, hydroxo, nitrato, nitrito, acetato and dichloroacetato or $R_2$ and $R_3$ taken together form a dinegatively charged bidentate ligand selected from the group consisting of sulfato, oxalato,

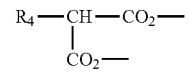

in which $R_4$ is hydrogen, hydroxyl, or an alkyl group of from one to four carbon atoms,

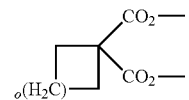

in which o is an integer from one to three and

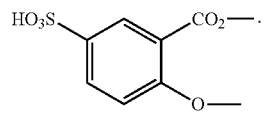

2. The method of claim 1 wherein R is —(CH$_2$)$_n$—, in which n is an integer from two to three; $R_1$ is hydrogen, carboxyl, an alkyl group of from one to four carbon atoms or an alkoxy group of from one to four carbon atoms; and $R_2$ and $R_3$ are negatively charged monodentate ligands which may be the same or different and are selected from the group consisting of chloro and bromo or $R_2$ and $R_3$ taken together form a dinegatively charged bidentate ligand selected from the group consisting of

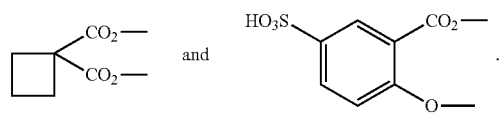

3. The method of claim 2 wherein $R_1$ is hydrogen, carboxyl, methyl, or methoxy.

4. The method of claim 1 wherein a compound of formula I is selected from the group consisting of:
[SP-4-2-(cis)]-dichloro(1,4-cyclohexanediamine-N,N') platinum;
[SP-4-2-(cis)]-dichloro(1,3-cyclopentanediamine-N,N') platinum;
[SP-4-2-(cis)]dichloro(1,4-cycloheptanediamine-N,N') platinum;
[SP-4-2-(cis)][1,1-cyclobutanedicarboxylato-(2-)O,O$^1$] (1,4-cyclohexanediamine-N,N')platinum;
[SP-4-2-(cis)]-(1,4-cyclohexanediamine-N,N') [2-hydroxy-5-sulfobenzoato (3)-O$^1$,O$^2$]platinate(1-),hydrogen; and
[SP-4-2-(cis)]-(1,4,cyclohexanediamine-N,N')[ethanedioato(2)-O,O$^1$]platinum.

5. The method of claim 4 wherein a compound of formula I is

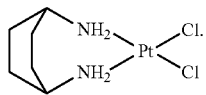

6. The method of claim 4 wherein a compound of formula I is

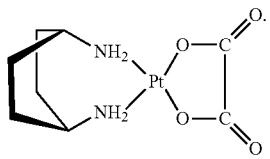

7. The method of claim 5 wherein the refractory colorectal cancer is oxaliplatin-refractory colorectal cancer.

8. The method of claim 7 wherein the mammal is a human.

9. The method of claim 6 wherein the refractory colorectal cancer is oxaliplatin-refractory colorectal cancer.

10. The method of claim 9 wherein the mammal is a human.

11. The method of claim 1 further comprising at least one second therapeutic agent useful in treating refractory colorectal cancer selected from the group consisting of: capecitabine; cetuximab; bevacizumab; a MEK inhibitor; a FOLFOX4 dosing schedule consisting of oxaliplatin, 5-fluorouracil and leucovorin; and a FOLFIRI dosing schedule consisting of irinotecan, 5-fluorouracil and leucovorin.

* * * * *